US012427222B2

(12) United States Patent
Freeman

(10) Patent No.: US 12,427,222 B2
(45) Date of Patent: *Sep. 30, 2025

(54) VAPORIZER DEVICE FOR HEALTH AND WELLNESS CARE

(71) Applicant: Bio Creative Enterprises, Costa Mesa, CA (US)

(72) Inventor: Jason P. Freeman, Newport Beach, CA (US)

(73) Assignee: BIO CREATIVE ENTERPRISES, Costa Mesa, CA (US)

( * ) Notice: Subject to any disclaimer, the term of this patent is extended or adjusted under 35 U.S.C. 154(b) by 853 days.

This patent is subject to a terminal disclaimer.

(21) Appl. No.: 17/454,932

(22) Filed: Nov. 15, 2021

(65) Prior Publication Data

US 2022/0072182 A1    Mar. 10, 2022

Related U.S. Application Data

(63) Continuation-in-part of application No. 16/135,899, filed on Sep. 19, 2018, now Pat. No. 11,203,033,
(Continued)

(51) Int. Cl.
*A61L 9/14* (2006.01)
*A61M 11/04* (2006.01)
(Continued)

(52) U.S. Cl.
CPC .............. *A61L 9/14* (2013.01); *A61M 11/042* (2014.02); *A61M 21/02* (2013.01);
(Continued)

(58) Field of Classification Search
CPC ... A61L 9/14; A61L 9/12; A61L 9/013; A61L 9/03; A61L 9/035; A61L 9/125;
(Continued)

(56) References Cited

U.S. PATENT DOCUMENTS 912,106 A    2/1909  Frazier
3,135,467 A  6/1964  Leo
(Continued)

FOREIGN PATENT DOCUMENTS

CN    203029678 U    7/2013
CN    103794003 A    5/2014
(Continued)

OTHER PUBLICATIONS

International Search Report & Written Opinion dated Feb. 1, 2023 from PCT Application No. PCT/US2022/079327.
(Continued)

*Primary Examiner* — Joseph D. Boecker
*Assistant Examiner* — Brian T Khong
(74) *Attorney, Agent, or Firm* — INNOVATION CAPITAL LAW GROUP, LLP; Vic Lin

(57) ABSTRACT

Methods and devices for atomizing a fragrant liquid can use a reservoir that receives a volume of a base liquid. One or more drops of a substance are added to the base liquid to form a volume of an aromatic liquid. A vaporizer atomizes the aromatic liquid, forming a mist that is emitted from the device. The device allows a user to customize the blend of substances that are used to form the aromatic liquid.

15 Claims, 31 Drawing Sheets

Related U.S. Application Data which is a continuation-in-part of application No. 15/977,341, filed on May 11, 2018, now abandoned.

(60) Provisional application No. 62/583,834, filed on Nov. 9, 2017, provisional application No. 62/572,184, filed on Oct. 13, 2017, provisional application No. 62/560,600, filed on Sep. 19, 2017.

(51) Int. Cl.
*A61M 21/02* (2006.01)
*B05B 17/06* (2006.01)
*A61M 21/00* (2006.01)

(52) U.S. Cl.
CPC . *A61L 2209/111* (2013.01); *A61M 2021/0016* (2013.01); *A61M 2205/3334* (2013.01); *A61M 2205/3379* (2013.01); *A61M 2205/3386* (2013.01); *A61M 2205/52* (2013.01); *A61M 2205/583* (2013.01); *A61M 2209/086* (2013.01); *A61M 2209/10* (2013.01); *B05B 17/0607* (2013.01)

(58) Field of Classification Search
CPC ........... A61L 2209/11; A61L 2209/132; A61L 2209/133; A61L 2209/111; A61L 2209/10; A61L 2209/13; A61L 2209/135; B05B 17/0646; B05B 17/0684; B05B 7/247; B05B 7/2472; B01F 3/04; A61M 11/005; B67D 1/0021; B67D 1/0015; B67D 1/0888; B67D 1/0085; B67D 1/0034

See application file for complete search history.

(56) References Cited

U.S. PATENT DOCUMENTS

| | | | |
|---|---|---|---|
| D365,628 S | 12/1995 | Braun | |
| D383,864 S | 9/1997 | Billings | |
| 5,725,125 A * | 3/1998 | Bessette | G01F 11/029 222/144.5 |
| 5,827,483 A | 10/1998 | Fullam | |
| 6,325,475 B1 * | 12/2001 | Hayes | A61M 11/042 604/28 |
| 6,371,451 B1 | 4/2002 | Choi | |
| D492,020 S | 6/2004 | Sevy | |
| D509,893 S | 9/2005 | Sevy | |
| 7,407,118 B2 | 8/2008 | Sevy | |
| 7,878,418 B2 | 2/2011 | Sevy | |
| D639,414 S | 6/2011 | Berndt | |
| 8,133,440 B2 | 3/2012 | Jörgensen | |
| 8,196,903 B2 | 6/2012 | Jörgensen | |
| 8,881,999 B2 | 11/2014 | Blaylock et al. | |
| 8,933,126 B2 | 1/2015 | Deminiere et al. | |
| 9,358,557 B2 | 6/2016 | Young et al. | |
| 9,421,295 B1 | 8/2016 | Li | |
| 9,439,995 B2 | 9/2016 | Conroy et al. | |
| D771,785 S | 11/2016 | Huang | |
| 9,511,389 B2 | 12/2016 | Teng et al. | |
| 9,517,286 B1 | 12/2016 | Li | |
| 9,623,137 B2 | 4/2017 | Chao et al. | |
| 9,715,223 B2 | 7/2017 | Chandler et al. | |
| 2007/0144455 A1 | 6/2007 | Ross et al. | |
| 2008/0011875 A1 | 1/2008 | Sipinski et al. | |
| 2008/0085103 A1 | 4/2008 | Beland et al. | |
| 2008/0230630 A1 | 9/2008 | Charpie | |
| 2008/0315005 A1 | 12/2008 | Michaels et al. | |
| 2010/0243754 A1 * | 9/2010 | Harris | A61L 9/14 239/34 |
| 2010/0309434 A1 | 12/2010 | Van Schijndel et al. | |
| 2010/0326117 A1 | 12/2010 | Hipp | |
| 2011/0268605 A1 | 11/2011 | Haran | |
| 2012/0175429 A1 | 7/2012 | Zupsic | |
| 2012/0325941 A1 | 12/2012 | Nakamoto et al. | |
| 2013/0213519 A1 | 8/2013 | Saloff et al. | |
| 2013/0247909 A1 | 9/2013 | Dotan | |
| 2013/0306752 A1 | 11/2013 | Ballesteros et al. | |
| 2013/0334336 A1 * | 12/2013 | Haran | A61L 9/14 239/102.1 |
| 2013/0334337 A1 * | 12/2013 | Haran | B05B 17/0684 239/303 |
| 2014/0014736 A1 | 1/2014 | Wirz | |
| 2014/0263723 A1 | 9/2014 | Hsiao | |
| 2014/0319238 A1 | 10/2014 | Su | |
| 2015/0100153 A1 | 4/2015 | Lin | |
| 2015/0117056 A1 | 4/2015 | Hsiao | |
| 2015/0367014 A1 | 12/2015 | Gruenbacher et al. | |
| 2016/0021325 A1 | 1/2016 | Porcar | |
| 2016/0106876 A1 | 4/2016 | Jih | |
| 2016/0331859 A1 | 11/2016 | Cameron | |
| 2016/0361452 A1 | 12/2016 | Blackley | |
| 2016/0361678 A1 | 12/2016 | Blackley | |
| 2017/0072086 A1 | 3/2017 | Gruenbacher et al. | |
| 2017/0076403 A1 | 3/2017 | Edwards et al. | |
| 2017/0182199 A1 | 6/2017 | Cardinal et al. | |
| 2017/0197004 A1 | 7/2017 | Kim | |
| 2017/0360981 A1 * | 12/2017 | Avidor | A61L 9/035 |
| 2019/0083719 A1 | 3/2019 | Freeman | |
| 2020/0276351 A1 | 9/2020 | Jin et al. | |

FOREIGN PATENT DOCUMENTS

| | | |
|---|---|---|
| CN | 205796105 U | 12/2016 |
| CN | 106904300 A | 6/2017 |
| CN | 106999972 A | 8/2017 |
| CN | 206734682 U | 12/2017 |
| CN | 207042704 U | 2/2018 |
| CN | 208927169 U | 6/2019 |
| JP | 2002052355 A | 2/2002 |
| KR | 1020180047393 A | 5/2018 |
| WO | 03084671 A1 | 10/2003 |
| WO | 2012101642 A2 | 8/2012 |
| WO | 2014176291 A1 | 10/2014 |
| WO | 2016098114 A1 | 6/2016 |
| WO | 2017079845 A1 | 5/2017 |
| WO | 2021185080 A1 | 9/2021 |

OTHER PUBLICATIONS

European Search Report dated May 10, 2021 from European Application No. EP18859628.
https://www.kickstarter.com/projects/1732003212/lumiere-smart-essential-oil-diffuser-for-wellbeing, 2017.
European Examination Report dated Jun. 5, 2024 from Application No. 18859628.2, 5 pages.

* cited by examiner

VAPORIZER DEVICE FOR HEALTH AND WELLNESS CARE

CROSS-REFERENCE TO RELATED APPLICATIONS

This application is a continuation-in-part of U.S. patent application Ser. No. 16/135,899, filed Sep. 19, 2018, which is a continuation-in-part of U.S. patent application Ser. No. 15/977,341, filed May 11, 2018, which claims the benefit of priority of U.S. provisional patent applications Nos. 62/583,834, filed Nov. 9, 2017, 62/572,184, filed Oct. 13, 2017 and 62/560,600, filed Sep. 19, 2017, the contents of each of which are herein incorporated by reference.

BACKGROUND OF THE INVENTION

1. Field of the Invention

This present disclosure relates generally to home health devices, and more particularly, relates to an essential oil diffuser that emits customizable fragrances.

2. Description of Prior Art and Related Information

Fragrances can promote feelings such as relaxation or stimulation. The inhaled aroma from natural oils or other plant materials is widely believed to stimulate brain function. Aromatherapy is an example of the use of fragrance to enhance psychological and physical well-being. Essential oils are volatile aroma compounds from plants. Essential oils can be atomized using a diffuser such as, for example, an ultrasonic diffuser. A user can insert or select a different essential oil into the diffuser to match the essential oil to the desired effect. For example, a user can select an essential oil that has a soothing effect if the user wishes to relax, or the user can select an essential oil that has a stimulative effect if the user wishes to become energized.

SUMMARY OF THE INVENTION

The systems, methods and devices described herein have innovative aspects, no single one of which is indispensable or solely responsible for their desirable attributes. Without limiting the scope of the claims, some of the advantageous features will now be summarized.

There is provided in accordance with one aspect of the present disclosure, a home health benefit device that includes a reservoir, a fragrance dock, a vaporizer, a duct, and a discharge tray. The reservoir is adapted to hold a foundation liquid. The fragrance dock is adapted to receive a container containing a fragrant liquid. The vaporizer is adapted to atomize a liquid. The vaporizer is configured to receive and vaporize at least a portion of the base liquid from the reservoir and at least a portion of the fragrant liquid from the container. The duct provides a fluid flow path between the vaporizer and an airspace that surrounds the fragrance diffuser. The discharge tray is adapted to receive an unused portion of a liquid mixture comprising the base liquid and the fragrant liquid. In some aspects, the fragrance diffuser includes a drop control mechanism configured to regulate the flow of the fragrant liquid from the container into the vaporizer. In some aspects, the fragrance diffuser includes a nasal cannula or an inhalation mask connected to the duct. In some aspects, the fragrance diffuser includes a transdermal applicator connected to the duct.

In one aspect of the present disclosure, a fragrance diffuser includes a reservoir, a plurality of docking stations, a droplet delivery system, a vaporizer, and a duct. The reservoir is adapted to receive a volume of a base liquid. Each of the plurality of docking stations is adapted to receive a container containing a fragrant liquid. The droplet delivery system is adapted to drop one or more droplets of the fragrant liquid into the volume of the base liquid in the reservoir. The vaporizer is adapted to atomize a liquid. The vaporizer is configured to receive and vaporize at least a portion of the aromatic liquid from the reservoir. The duct provides a fluid flow path between the vaporizer and an airspace that surrounds the fragrance diffuser.

In some aspects, the fragrance diffuser includes a vaporizer disposed at a bottom of the reservoir. In some aspects, the fragrance diffuser includes a removable insert that fits into the reservoir and holds the foundation liquid. The removable insert is adapted to facilitate cleaning of the fragrance diffuser by allowing the removable insert to be removed from a base portion of the fragrance diffuser and cleaned separately from the fragrance diffuser. In some aspects, the fragrance diffuser is configured to run a cleaning cycle. In some aspects, the cleaning cycle cleans an internal component of the droplet delivery system. In some aspects, the internal component cleaned by the cleaning cycle is a portion of tubing. In some aspects, the fragrance diffuser includes a mixer that mixes the fragrant liquid drops with the foundation liquid. In some aspects, the vaporizer is a piezoelectric device. In some aspects, the piezoelectric device mixes the fragrant liquid drops with the foundation liquid. In some aspects, the piezoelectric device is disposed at the bottom of the removable insert. In some aspects, the fragrance diffuser includes a vaporizer at the bottom of the removable insert, with the vaporizer electrically coupled to one or more conductors disposed on an outer surface of the removable insert, the one or more conductors being arranged to establish an electrical contact between the vaporizer and a base portion of the fragrance diffuser when the removable insert is seated into a base portion of the diffuser.

In one aspect of the present disclosure, a method of nebulizing an aromatic liquid is provided. The method includes receiving in a processor information for a desired blend of one or more liquid ingredients; sending from the processor a signal to a reservoir valve to actuate the reservoir valve such that a portion of a reservoir liquid in a reservoir flows through the reservoir valve and into an atomizing chamber; sending from the processor a signal to a port valve to actuate the port valve such that a portion of a concentrate liquid in a container connected to the port valve flows through the port valve and into the atomizing chamber; combining the portion of the reservoir liquid with the portion of the concentrate liquid to form a blended liquid; atomizing the blended liquid to create a vapor; and conveying the vapor through a duct that communicates between the atomizing chamber and an exterior of the reservoir.

In some aspects, the method of nebulizing an aromatic liquid includes draining a remaining portion of the blended liquid from the atomizing chamber and an exterior of the reservoir. In some aspects the method of nebulizing an aromatic liquid includes, sending from the processor a signal to a port valve includes sending from the processor a first signal to a first port valve to actuate the first port valve such that a first portion of a first concentrate liquid in a first container connected to the first port valve flows through the first port valve and into an atomizing chamber; and sending from the processor a second signal to a second port valve to actuate the second port valve such that a second portion of a second concentrate liquid in a second container connected to the second port valve flows through the port valve and into an atomizing chamber; wherein combining the portion of the reservoir liquid with the portion of the concentrate liquid to form a blended liquid includes combining the first portion of the first concentrate liquid with the second portion of the second concentrate liquid and with the portion of the reservoir liquid.

In one aspect of the present disclosure, a method of ultrasonically atomizing an aromatic liquid is provided. The method includes receiving into a reservoir a volume of a base liquid; dropping one or more drops of a substance into the volume of the base liquid to form a volume of the aromatic liquid; receiving a portion of the volume of the aromatic liquid into an atomization chamber; and atomizing ultrasonically within the atomization chamber the portion of the volume of the aromatic liquid. In some aspects, dropping one or more drops is controlled by a processor that sends a signal to a motor to control a volume of each of the one or more drops.

DETAILED DESCRIPTION OF THE PREFERRED EMBODIMENTS AND BEST MODE OF INVENTION

Broadly, embodiments of the present invention provide methods and devices for atomizing a fragrant liquid that can use a reservoir that receives a volume of a base liquid. One or more drops of a substance are added to the base liquid to form a volume of an aromatic liquid. A vaporizer atomizes the aromatic liquid, forming a mist that is emitted from the device. The device allows a user to customize the blend of substances that are used to form the aromatic liquid. The methods and devices may be used for general fragrance or for providing a home health benefit by disbursing a chemical, medicine and/or fragrance from the device. For example, for relaxation, lavender essential oil may be dispensed along with CBD oil to provide a medicinal fragrance for relaxation of the user.

In addition to providing the fragrance, medicine and/or chemical delivery, the device may emit a light for red light therapy or other similar light therapy. Further, a sanitizing lamp, such as a UV-C lamp, may be provided inside the device, along an air flow path, to help clean and sanitize air. Air quality sensors may be included to alert the user of low air quality, to adjust a fan speed, provided additional fragrance or air purification additives, or the like.

The device can be used in various therapeutic environments. For example, the device can be recommended by doctors for patients who are autistic, PTSD, depressed, or the like. Attachments can be added to the device for direct inhalation or derma application for use on the skin, for example.

Figure 1:
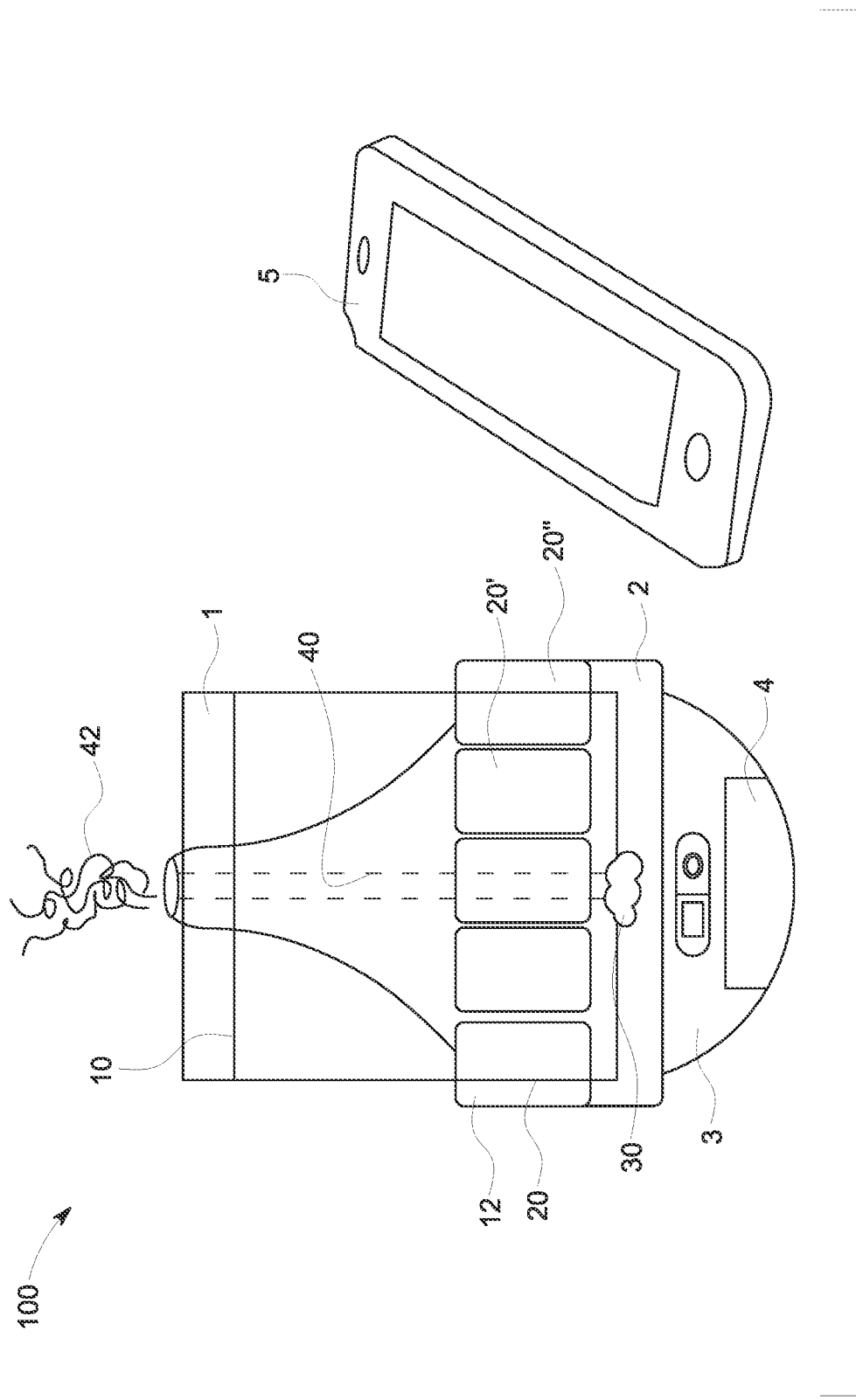
FIG. 1 is an embodiment of an essential oil diffuser illustrating that the diffuser can be controlled or monitored by a mobile device.

FIG. 1 illustrates an embodiment of a diffuser system 100 according to the present disclosure. As will be described below, in certain embodiments and modes of operation the diffuser system 100 advantageously allows a user to customize the blend of essential oils that the diffuser system atomizes. The diffuser system 100 can be used to vaporize or atomize an aromatic liquid, which in certain embodiments can include an essential oil. The diffuser system 100 can vaporize or atomize a liquid to form a fog, a mist, or an aerosol. For purposes of the present disclosure, an aerosol can be a mixture of gas and solid or liquid particles. The diffuser system 100 can produce an aerosol having liquid droplets that are small (e.g., 511 m diameter). In some embodiments, the diffuser system 100 can produce an aerosol comprising liquid droplets that have a diameter of a size of about: 211 m, 511 m, 1011 m, 1511 m, 3011 m, 10011 m, or a value between any of the aforementioned sizes. While the embodiments of the diffuser system 100 are described in the context in which the diffuser system 100 is used to vaporize or atomize an essential oil, it is anticipated that the diffuser system 100 can be used to vaporize or atomize other substances such as chemicals (e.g., nicotine, Cannabidiol (CBD) oil, or the like) or pharmaceuticals (e.g., corticosteroids, bronchodilators, or the like). The diffuser system 100 can use a nebulizing component, an ultrasonic atomizer, a piezo diffusion vaporizer technology, or other mechanisms to convert a liquid into a vapor, an aerosol, or a gas. The nebulizing component can be powered by mechanical or electrical device. The nebulizing component can be a vibrating mesh nebulizer, a jet air nebulizer, an ultrasonic wave nebulizer, or other nebulizing means known in the art. As noted above, in addition to essential oils and other aromatic liquids the diffuser system 100 can be used to vaporize or atomize a drug or a chemical, allowing the diffuser system 100 to be used as a delivery device as well.

As shown in FIG. 1, the diffuser system 100 can include a reservoir 1. The reservoir 1 can be adapted to hold a foundation liquid 10 (e.g., water). The diffuser system 100 can include a docking station 2. The docking station 2 can be adapted to receive one or more containers 12 that contain a concentrate liquid 20. The concentrate liquid 20 can be an essential oil. The concentrate liquid 20 can also be a liquid other than an essential oil. The docking station 2 can be adapted to receive a first concentrate liquid 20' that is a first type of concentrate liquid 20 (e.g., lavender essential oil) and a second concentrate liquid 20" that is a second type of concentrate liquid 20 (e.g., eucalyptus essential oil) that is different from the first type of concentrate liquid 20'. In some embodiments, the diffuser system 100 mixes the foundation liquid 10 with one or more of the concentrate liquids 20. In some embodiments, the diffuser system 100 mixes a first concentrate liquid 20' with a second concentrate liquid 20". The diffuser system 100 can mix a first concentrate liquid 20' with a second concentrate liquid 20" with or without including the foundation liquid 10 in the mixture.

The diffuser system 100 can include a main tank or atomization chamber 3 that receives a mixture of the concentrate liquid 20. The atomization chamber 3 can receive a mixture of the concentrate liquid 20 and the foundation liquid 10. The atomization chamber 3 can receive a mixture of a blend of different types of concentrate liquid 20', 20" and the foundation liquid 10. The atomization chamber 3 can receive a mixture of a blend of different types of concentrate liquid 20',20" without receiving the foundation liquid 10.

The diffuser system 100 can include a vaporizer 30. The vaporizer 30 can be adapted to vaporize a liquid into a gas, an aerosol, or a vapor. The vaporizer 30 can receive and vaporize a liquid mixture of the concentrate liquid 20 and the foundation liquid 10. The vaporizer 30 can include a nebulizing component, an ultrasonic atomizer, a piezo diffusion vaporizer technology, or other mechanisms to convert a liquid into an aerosol, a vapor, or a gas. The diffuser system 100 can include a duct 40 that provides a flow path between the vaporizer 30 and the outside airspace surrounding the diffuser system 100. The duct 40 can provide a flow path that allows a vapor 42 produced by the vaporizer 30 to exit the diffuser system 100.

The diffuser system 100 can include a discharge tray 4. The discharge tray 4 can be adapted to receive a portion of a liquid mixture that has not been vaporized by the vaporizer 30. An unused portion of a mixture of the concentrate liquid 20 and the foundation liquid 10 that has not been vaporized by the vaporizer 30 can be drained into the discharge tray 40, thereby preventing or reducing cross-contamination between mixtures. After selecting another mixture, the leftover foundation liquid 10 and concentrate 20 mixture can be drained into the discharge tray 4. The discharge tray 4 can include a seal that prevents or reduces the aroma of a liquid within the discharge tray 4 from reaching the airspace that surrounds the diffuser system 100.

The diffuser system 100 can be controlled or monitored by a mobile device 5. The diffuser system 100 can be controlled or monitored by an application software (also referred to herein as "mobile app") that is run on the mobile device 5. The mobile app can provide the following functionalities: power on or off the diffuser system 100; choose a mixture for the diffuser system 100 to vaporize; monitor levels of the foundation liquid 10 and the concentrate liquid 20; purchase refills of the concentrate liquid 20; provide educational information (e.g., information on essential oils); create, customize, and formulate different mixtures; alert the user when the diffuser system 100 should be cleaned. The delivery system 100 can include a computer (not shown) configured to receive data from the mobile device 5. The delivery system 100 can have a computer with WI-FI® or BLUETOOTH® capability, allowing the delivery system 100 to communicate with a mobile device 5. The diffuser system 100 can include a processor that controls the addition of the concentrate 20 to the foundation liquid 10. The processor can receive a signal from a mobile device 5. The processor can send a signal to a component of the diffuser system 100 to modify or initiate an operation of the diffuser system 100 (e.g., activate a flow of concentrate 20). The processor can send the signal to the component based on the signal the processor receives from the mobile device 5. The mobile device 5 can be used to turn on the diffuser system 100. The mobile device 5 can be used to customize or select fragrance recipes to run on the diffuser system 100. For example, a user can select a fragrance recipe on the mobile device 5. The mobile device 5 can then send a signal to the processor to inform the processor of the recipe selection. The processor can send a signal to a droplet delivery system (discussed below in more detail) of the diffuser system 100E. The droplet delivery system can respond to the signal received from the processor by operating to dispense an amount of concentrate 20 that corresponds to the received signal.

Figure 7:
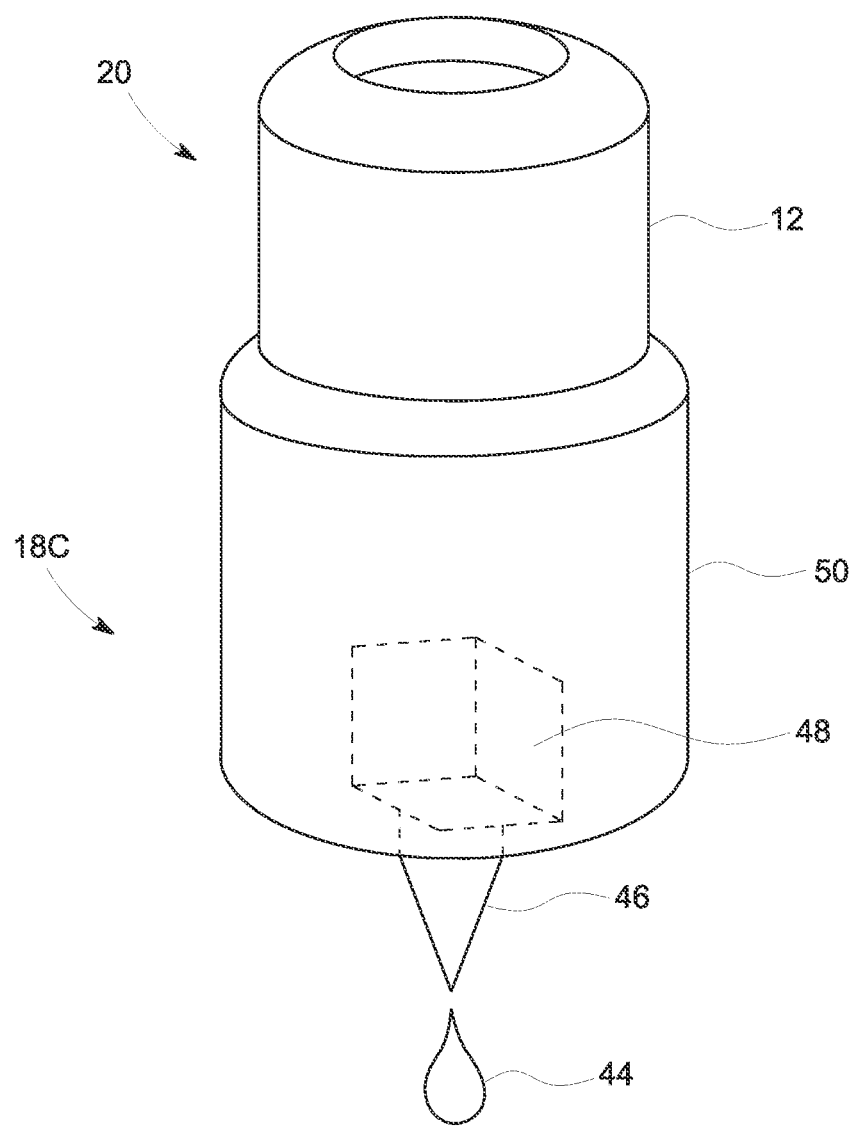
FIG. 7 shows an embodiment of a drop control mechanism associated with the essential oil diffuser system of the present disclosure.
Figure 18:
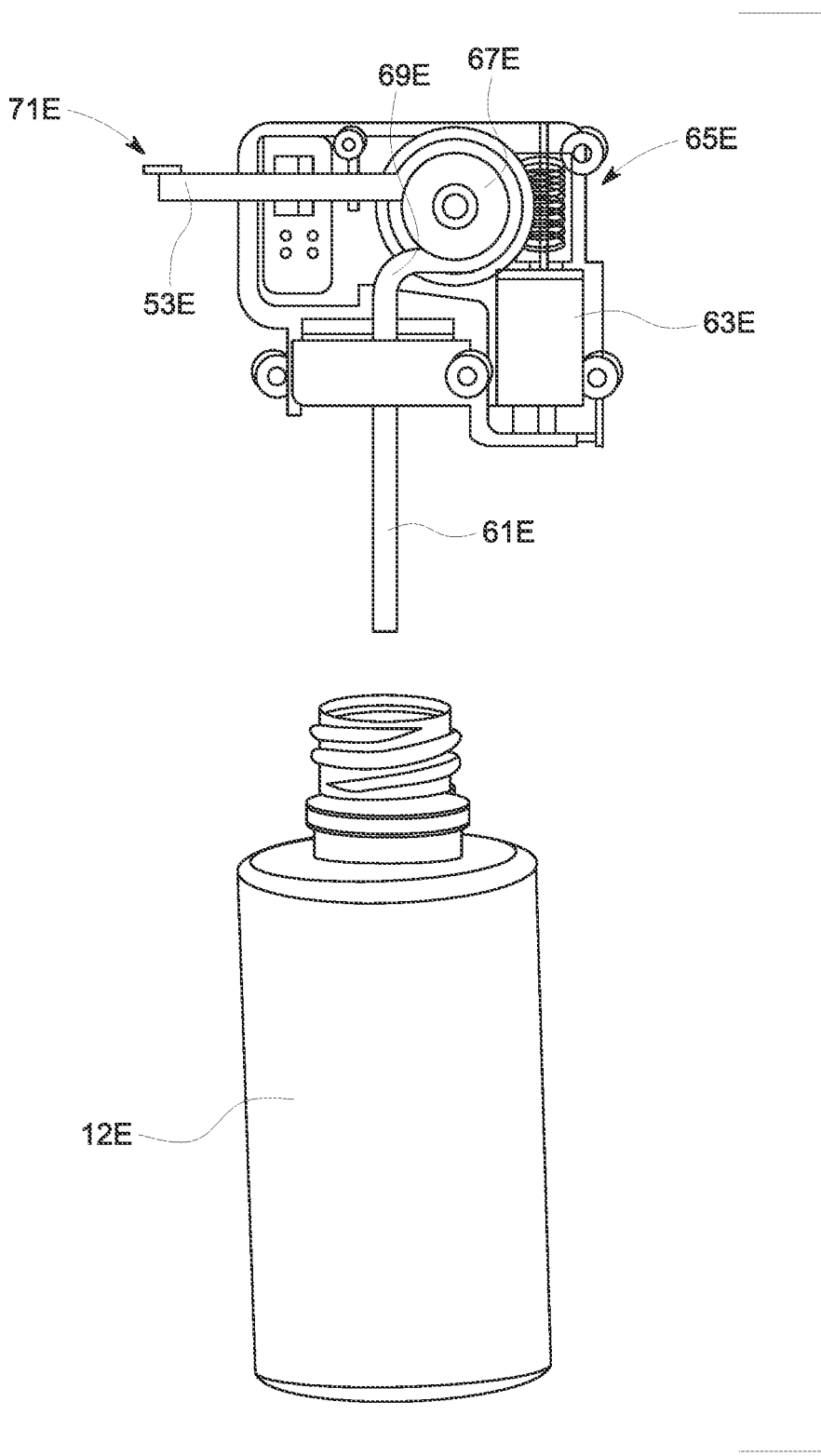
FIG. 18 is a side view of a droplet delivery system of the docking station of FIG. 17.
Figure 19:
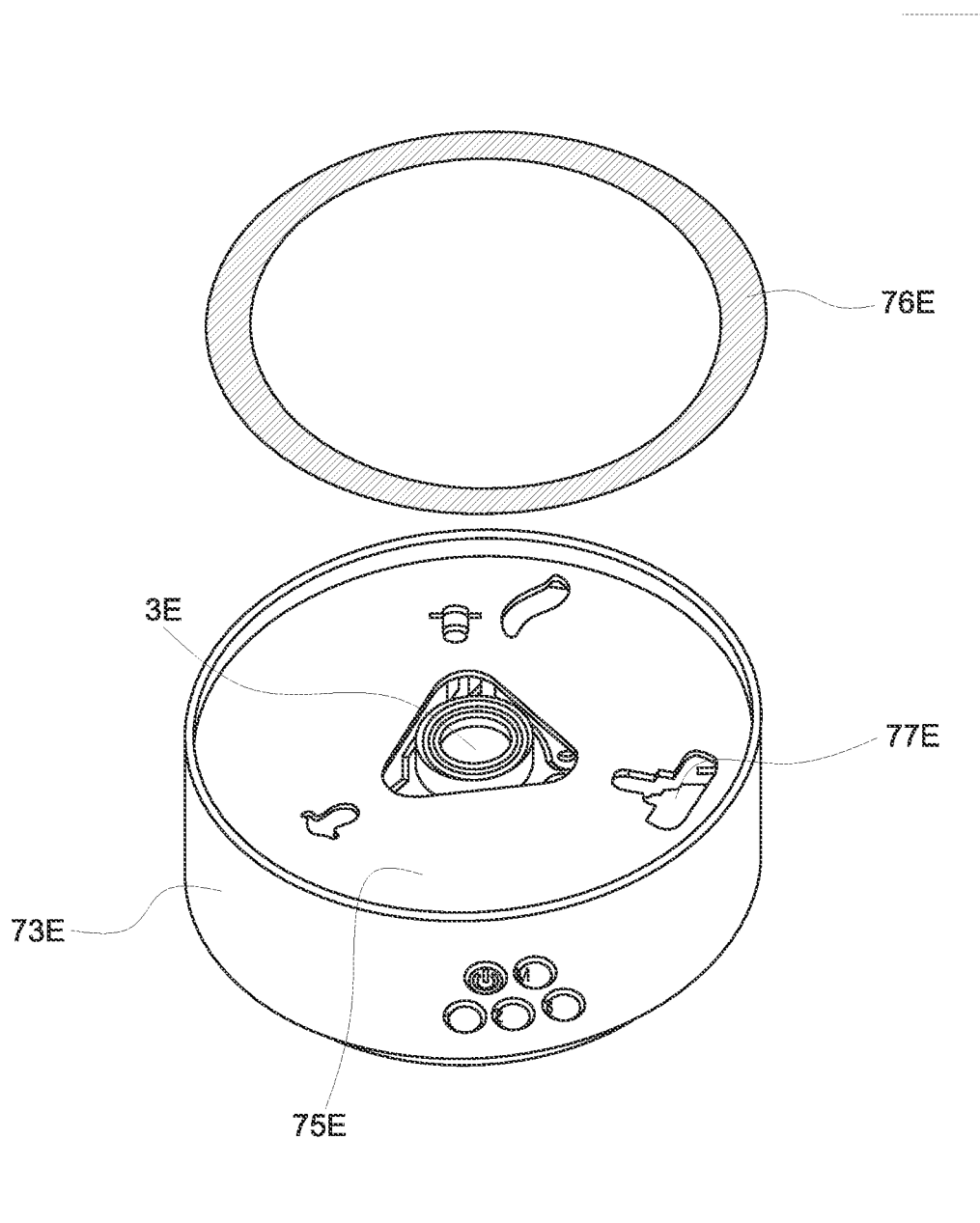
FIG. 19 is a top perspective view of a base and light ring of the essential oil diffuser system of FIG. 13A.
Figure 20:
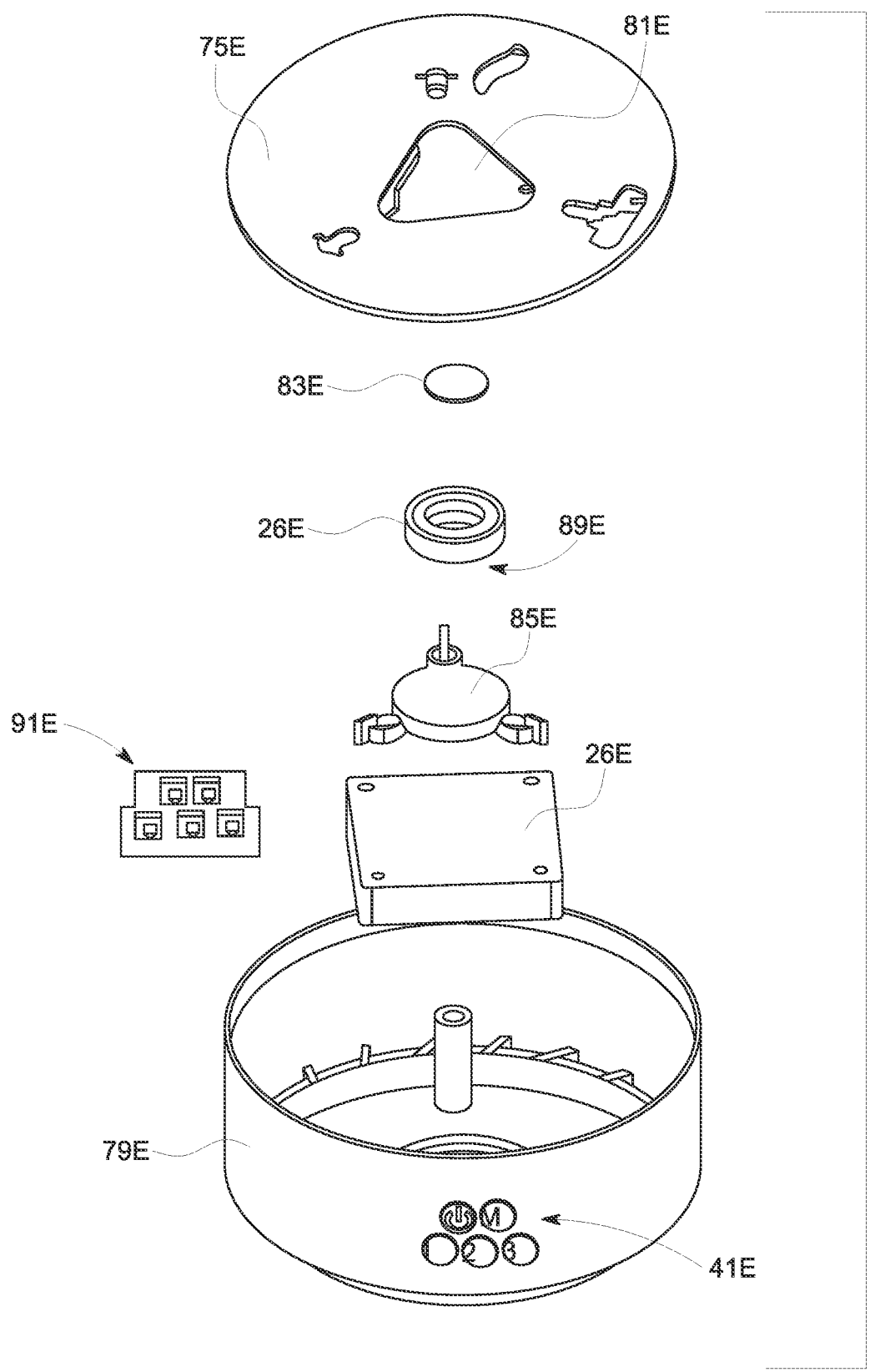
FIG. 20 is an exploded view of the base of FIG. 19.

The diffuser system 100E can be adapted to run a cleaning cycle after the diffuser system 100E has been run for a certain number of times or has met another condition that triggers the cleaning cycle. The trigger event of the cleaning cycle can be set by the user or the mobile application. The mobile application and the diffuser system 100E can work together to communicate to the user when the diffuser system 100E should be cleaned. In some embodiments, the diffuser system 100E or the mobile application will keep track of the number of times the diffuser system 100E has powered on the vaporizer 30. After a certain threshold number of uses is reached, the application can notify the user to clean the vaporizer 30 or other component of the diffuser system 100E. In some embodiments, the diffuser system 100E can run a clean cycle to clean the inner tubes of the essential oil droplet delivery system (FIGS. 7, 8, and 18). In some embodiments, the application can keep track of the number of times the essential oil droplet delivery system delivers a drop. Once a threshold number of drops has been delivered, the user can be directed to run a cleaning cycle. In some embodiments, the user can purchase a cleaning mixture that can be screwed into each droplet delivery system (e.g., pump). A function in the application can set the diffuser system 100E in a cleaning cycle state in which the droplet delivery system will pull in the cleaning solution to lubricate and clean the inner components (e.g., tubing) of the droplet delivery system.

The container 12 that contains the concentrate liquid 20 can be an oil jar that is placed or screwed into the docking station 2. The container 12 can include a small magnetic strip or other identifier that allows the diffuser system 100 to identify the type of concentrate liquid 20 that is contained within the container 12. The diffuser system 100 can be arranged to send data to the mobile device 5 to inform the mobile app the type of concentrate liquids 20 that are attached to the docking station 2. The mobile app can communicate data to the diffuser system 100 to instruct the diffuser system 100 which concentrate liquids 20 to mix. A user can select a pre-programmed mixture of concentrate liquids 20. In some embodiments, the diffuser system 100 allows a user to customize a mixture of concentrate liquids 20. For example, a user can customize a mixture of concentrate liquids 20 by specifying volumes and identities of different concentrate liquids 20 that are attached to the docking station 2 of the diffuser system 100. The diffuser system 100 can allow different combinations of concentrate liquids (e.g., essential oils) to be mixed or blended. The diffuser system 100 can allow a single concentrate liquid 20 to be used separately, i.e., without mixing with different types of concentrate liquids 20. In some embodiments, the concentrate liquid 20 is a pre-mixed concentrate. The diffuser system 100 can be arranged to mix a pre-mixed concentrate liquid 20 from a single container 12 with the foundation liquid 10.

Figure 2:
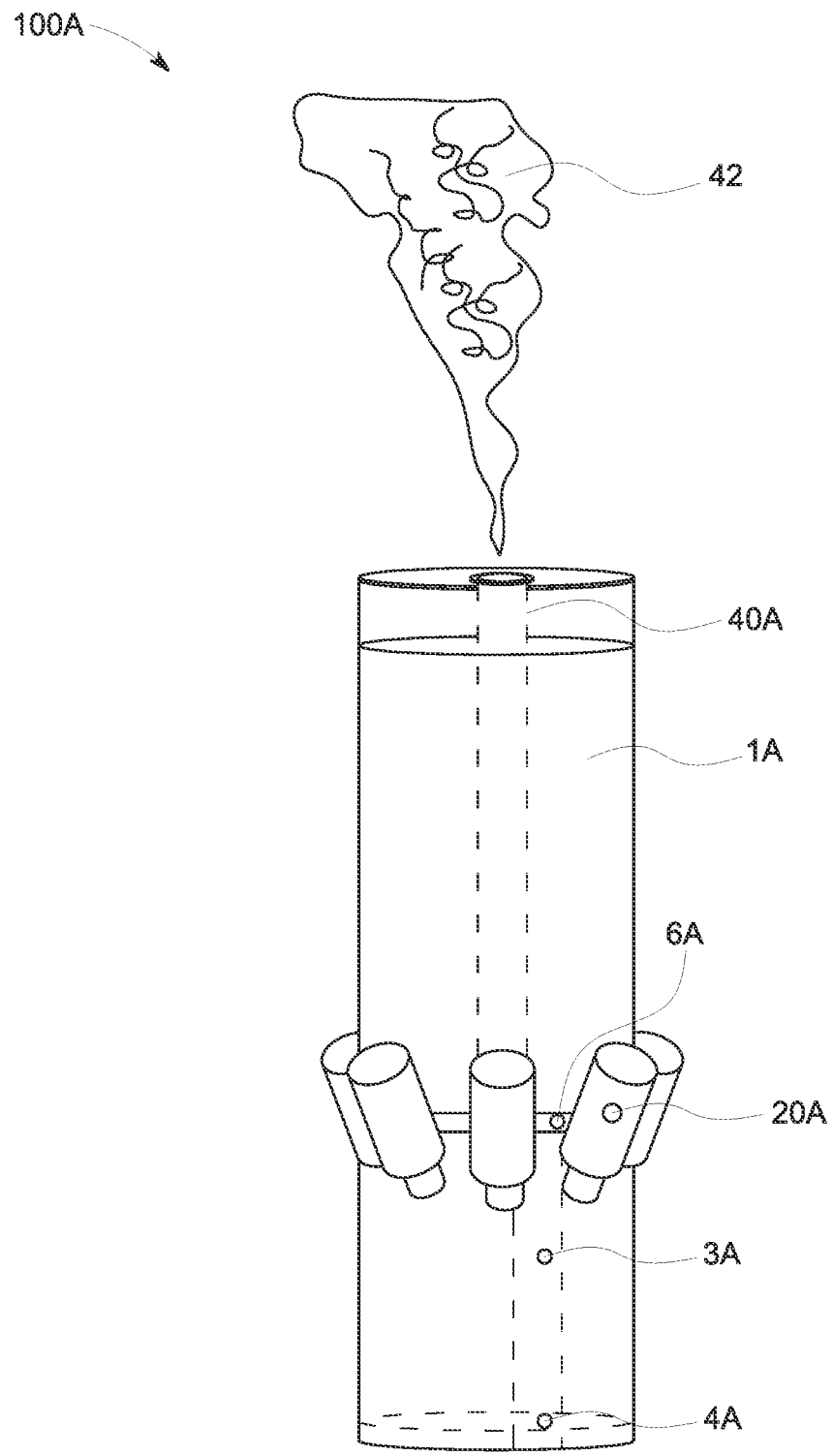
FIG. 2 is another embodiment of an essential oil diffuser.

FIG. 2 illustrates another embodiment of a diffuser system 100A similar to the diffuser system 100 except as described differently below. The features of the diffuser system 100A can be combined or included with the diffuser system 100 or any other embodiment discussed herein. The diffuser system 100A can include a reservoir 1A, a concentrate liquid 20A, an atomization chamber 3A, a discharge tray 4A, and a duct 40A, as described above. The illustrated embodiment also includes a light source 6A. The light source 6A can be a bright LED, such as a RGB NEOPIXEL® LED or other light source. The diffuser system 100A can cycle the intensity or color of the light source 6A to create a soothing aesthetic effect. The diffuser system 100A can include a quiet fan (shown in FIG. 3) that facilitates or enhances delivery of vapor 42 through the duct 40A.

A non-limiting, illustrative method of use of the diffuser system 100A will now be described. The diffuser system 100A can be arranged as a smart essential oil and water atomization diffuser. The system 100A can hold a plurality of essential oil containers. In some embodiments, the diffuser system 100A can hold up to six essential oils in 10 mL bottles. The diffuser system 100A can identify the scent and brand of the essential oil bottle using a Quick Response (QR) scanner built into each essential oils compartment when placed into the diffuser. The diffuser will also keep track of the water levels.

Using a mobile app, the user can choose a mixture option provided by the mobile application based on the oils that are present in the diffuser. The system 100A can allow users to also create their own mixture. In some embodiments, the mobile app can allow a user to mix a pre-mixed concentrate liquid 20 from a first container 12 with the foundation liquid 10.

The water reservoir 1A shown in FIG. 2 will hold the water. When the user chooses a mixture blend, the user can also specify the amount of time that the diffuser system 100A will be on. Based on the selection, the exact amount of water will be pumped into the atomization chamber 3A along with the correct number of drops from the essential oil bottle.

A water atomizer will atomize the mixture and a quiet mini fan will force the atomized water out of the diffuser system 100A. Bright LEDs 6A will shine through the water reservoir 1A, setting the mood.

The user will be alerted when the water reservoir 1A is low on water. If the user decides to cancel the current mixture that is being diffused, the mixture will be drained into a mixture disposal holder such as the discharge tray 4A. The water reservoir 1A can be removable. The discharge tray 4A can also be removable to pour out the unused portion of the mixture. In some arrangements, the diffuser system 100A can allow a user to pass a volume of water from the water reservoir 1A through the atomizing chamber 3A in order to rinse or clean the diffuser system 100A before a new mixture is created within the atomizing chamber 3A.

The diffuser system 100A can communicate with a content management system web application to input education information, new mixtures, or other content onto an application programming interface (API). The mobile app can be supported on an operating system, such as iOS™ or ANDROID™ and can pull in this data using the API and present the user with a selection of mixtures that are available. The app will categorize the mixtures into different moods. A mood will represent a mixture and a LED light color to accompany the mood.

The essential oil bottles can have special labels that the QR reader on the diffuser system 100A will be able to scan automatically after placing the bottle into its compartment. Refills can be purchased using the mobile app.

The diffuser system 100A can use water and ultrasound to atomize the essential oil and water mixture. The diffuser system 100A can be adapted to receive multiple standard or generic sized essential oil bottles. The diffuser system 100A can include adapters that allow various sizes or configurations of essential oil bottles to be attached to the diffuser system 100A. The essential oil bottles can be placed on the outside of the diffuser system 100A.

Figure 3:
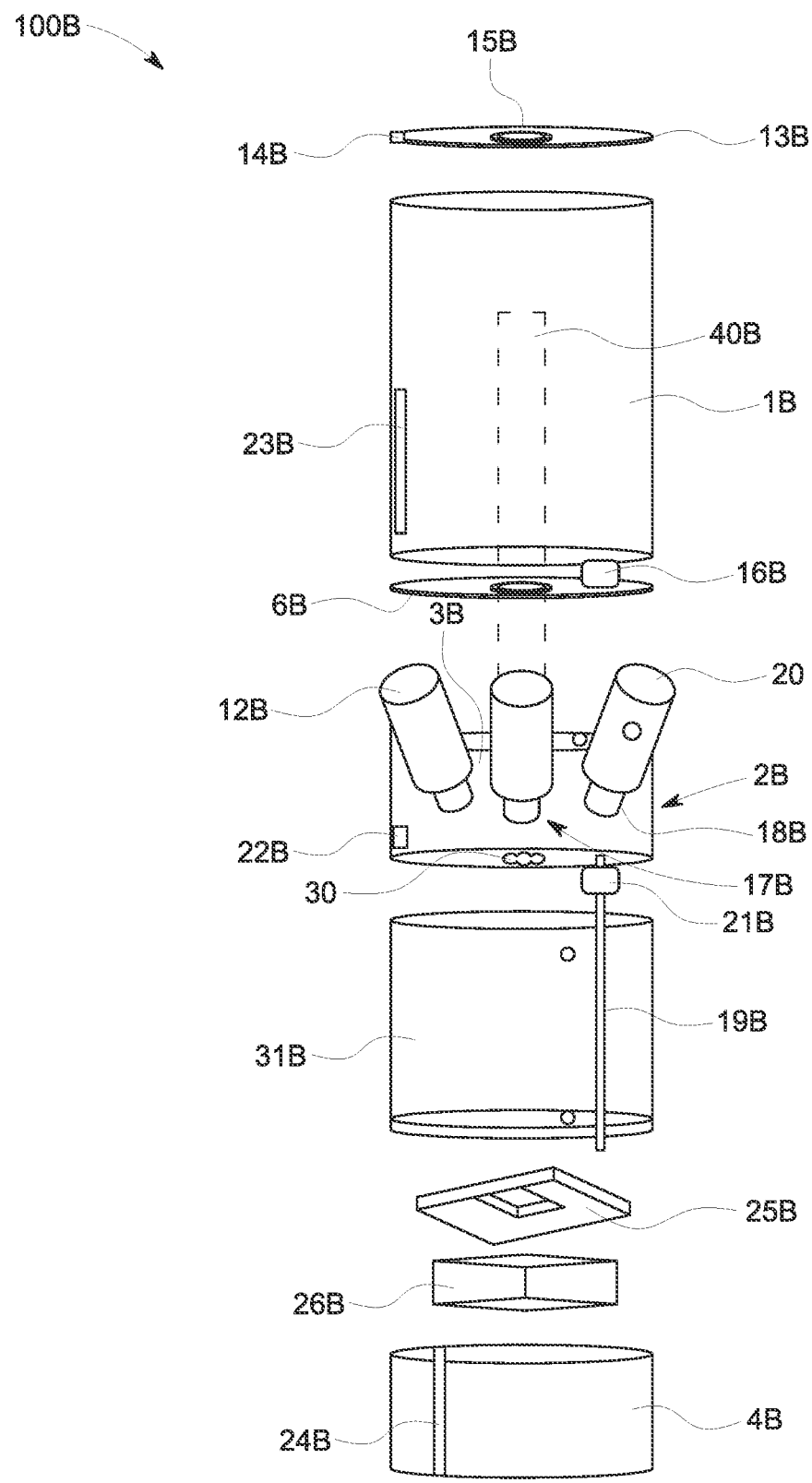
FIG. 3 is an assembly view of the embodiment of an essential oil diffuser shown in FIG. 2.

FIG. 3 illustrates an assembly view a diffuser system 100B similar to the diffuser system 100A except as described differently below. The features of the diffuser system 100B can be combined or included with the diffuser system 100A or any other embodiment discussed herein. For ease of description, a reference system will be defined for the diffuser system 100B. The 'bottom" of the diffuser system 100B refers to the surface of the diffuser system 100B that contacts a supporting surface. The "top" of the diffuser system 100B is the surface of the diffuser system 100B that is opposite the bottom of the diffuser system 100B. In the illustrative embodiment shown in FIG. 3, the diffuser system 100B has a substantially cylindrical form. An "inner" surface of the diffuser system 100B is a surface that faces the longitudinal axis of the substantially cylindrical form of the diffuser system 100B. An "outer" surface is a surface that faces away from the longitudinal axis. The reference system is intended to be non-limiting, and the diffuser system 100B can be arranged in configurations that do not conform to the illustrative reference system described herein.

With continued reference to FIG. 3, the diffuser system 100B can include a reservoir 1B adapted to hold water or other foundation liquid for mixing with essential oils to create a mixture for nebulizing, as described previously. The diffuser system 100B can include a lid 13B located at the top of the reservoir 1B. The lid 13B can be removed from the top of the reservoir 1B to allow access to the interior space of the reservoir 1B. In some configurations, the lid 13B can include a hinge 14B that connects the lid 13B to the reservoir 1B. The hinge 14B can allow the lid 13B to be flipped open to allow a user to refill or change the liquid housed within the internal space of the reservoir 1B. In some embodiments, the lid 13B includes a locking clasp or other fastening device to secure the lid 13B onto the reservoir 1B in the closed position. In certain arrangements, the lid 13B does not include a hinge 14B, allowing the lid 13B to be completely separated from the reservoir 1B. The lid 13B can be secured to the top of the reservoir 1B by a threaded connection. For example the outer periphery of the lid 13B can include an external thread that mates with an internal thread on the inner surface and at the top of the reservoir 1B. The diffuser system 100B can use a pin-and-groove connection feature to secure the lid 13B and the reservoir 1B. For example, a pin located on the periphery of the lid 13B can be advanced longitudinally within a groove on the inner surface of the reservoir 1B and then rotated circumferentially about the longitudinal axis to lock the pin in the groove.

The lid 13B can include a central opening 15B that provides a flow path across the lid 13B when the lid 13B is closed over the top of the reservoir 1B. The central opening 15B can align with the duct 40B when the lid 13B is closed over the top of the reservoir 1B. The lid 13B can include one or more seals that form a seal between the lid 13B and the reservoir 1B. For example, the lid 13B can have a duct seal positioned around the central opening 15B on the reservoir-facing surface of the lid 13B. The duct seal can form a seal between the lid 13B and the duct 40B when the lid 13B is in the closed position. The lid 13B can have a peripheral seal at the outer periphery of the reservoir-facing surface of the lid 13B. The peripheral seal can form a seal between the lid 13B and the top opening of the reservoir 1B when the lid 13B is in the closed position. In some embodiments, the lid 13B can have a single seal that extends across the entire reservoir-facing surface of the lid 13B and forms seals with both the duct 40B and the top opening of the reservoir 1B when the lid 13B is in the closed position. The lid 13B can be arranged to form a substantially water tight seal with the top of the reservoir 1B, thereby preventing or reducing water within the reservoir 1B from spilling out of the reservoir 1B if the diffuser system 100B is inverted or oriented on its side.

The diffuser system 100B can have a duct 40B similar to the duct 40A except as described differently below. The duct 40B can extend longitudinally within the reservoir 1B to provide a flow path between the atomization chamber 3B and the outside environment. The duct 40B can be a bypass molded into the reservoir 1B. The reservoir 1B can include one or more buttresses or support structures that extend from the inner surface of the reservoir 1B to the outer surface of the duct 40A. The duct 40B can be molded into a component of the diffuser system 100B other than the reservoir 1B. For example, the duct 40B can be molded into the atomization chamber 3B and extend within the reservoir 1B from a top surface of the atomization chamber 3B toward the top of the reservoir 1B. The duct 40B can all certain configurations, the diffuser system 100B can be a larger or smaller size than the illustrated embodiment. The diffuser system 100B can be any dimension in size as well as hold any size essential oil bottles. For example, the diffuser system 100B can be a mini-sized diffuser system that holds six small containers 12 of essential oil, with the capacity of each of the small containers 12 being less than 10 mL (e.g., 2 mL). The diffuser system 100B can be an extra-large diffuser system 100B that holds six large containers 12 of essential oil, with the capacity of each of the large containers 12 being more than 10 mL (e.g., 25 mL).

In the illustrated embodiment, the container 12B is jar shaped and attached to the docking station 2B by inserting a mouth of the container 12B into a port 17B of the diffuser system 100B. The port 17B can include a port valve 18B adapted to pump or control flow of liquid from the container 12B into the atomization chamber 3B. The port valve 18B can be a mini-solenoid valve that opens to allow the concentrate liquid 20 within the container 12B to flow through the port valve 18B and into the atomization chamber 3B. In some configurations, flow through the port valve 18B is gravity driven. In some arrangements, the port valve 18B can include a pump (e.g., diaphragm pump) that actively pumps concentrate liquid 20 into the atomization chamber 3B from the container 12B.

As discussed above, the diffuser system 100B can identify the contents of a container 12B attached to a port 17B. For example, the container 12B can include an identification module (e.g., RFID tag, magnetic strip, QR code) on or near the mouth of the container 12B. The port 17B can include a reading means (e.g., RFID scanner, magnetic scanner) adapted to read the identification module on the container 12B. The reading means can be configured to communicate the information of the contents of the container 12B to a central processing unit (CPU) or memory device of the diffuser system 100B. In some embodiments, the identification module on the container 12B can be scanned using a mobile device 5. For example, a user can scan a QR code on a container 12B with a mobile device 5 using the mobile application to identify the contents of the scanned container 12B. The mobile application can be configured to allow a user to order additional quantities of a scanned container 12B.

The diffuser system 100B can include a discharge tray 4B similar to the discharge tray 4A except as described differently below. The discharge tray 4B can receive and hold liquid mixtures that were not completely nebulized in the atomization chamber 3B. When the diffuser system 100B is interrupted before the liquid mixture in the atomization chamber 3B has been fully atomized, there will be some remaining mixture liquid in the atomization chamber 3B. The diffuser system 100B can be adapted to allow this remaining mixture liquid to be removed from the atomization chamber 3B before another customized mixture is introduced into the atomization chamber 3B, thereby preventing a remaining portion of a previous mixture from contaminating a subsequent mixture introduced into the atomization chamber 3B. The discharge tray 4B can be removable, allowing a user to dispose of the discharged liquid and clean the discharge tray 4B.

The diffuser system 100B can include a discharge tube 19B that communicates between the atomizing chamber 3B and the discharge tray 4B. The discharge tube 19B can provide a flow path for liquid to flow from the atomizing chamber 3B to the discharge tray 4B. The diffuser system 100B can include a discharge valve 21B adapted to pump or control flow of liquid from the atomizing chamber 3B into the discharge tray 4B. The discharge valve 18B can be a mini-solenoid valve that opens to allow liquid to flow through the discharge valve 18B and into the discharge tray 4B. In some configurations, flow through the discharge valve 18B is gravity driven. In some arrangements, the discharge valve 18B can include a pump (e.g., diaphragm pump) that actively pumps liquid into the discharge tray 4B from the atomizing chamber 3B.

The atomizing chamber 3B can include an atomizing liquid sensor 22B. The atomizing liquid sensor 22B can detect the presence of a liquid in the atomizing chamber 3B, such as, for example, through a change in the resistivity of the atomizing liquid sensor 22B. If liquid is detected in the atomizing chamber 3B, the discharge valve 18B can be activated to drain or pump the liquid from the atomizing chamber 3B before a new mixture is created in the atomizing chamber 3B. In some configurations, the diffuser system 100B can be arranged to rinse the atomizing chamber 3B before a new mixture is created. For example, the diffuser system 100B can flow a portion of water from the reservoir 1B into the atomizing chamber 3B and then drain the water through the discharge tube 19B to the discharge tray 4B before creating a new mixture in the atomizing chamber 3B.

The diffuser system can include a reservoir liquid sensor 23B. In the illustrated embodiment, the reservoir liquid sensor 23B is positioned on an inside surface of the reservoir 1B and longitudinally aligned with a longitudinal axis of the substantially cylindrical reservoir 1B. The reservoir liquid sensor 23B can detect the presence of a liquid in the reservoir 1B, such as, for example, through a change in the resistivity of the reservoir liquid sensor 23B. The reservoir liquid sensor 23B can communicate the reading of the reservoir liquid sensor 23B to a central processing unit (CPU) or memory device of the diffuser system 100B. In some arrangements, if the reservoir liquid sensor 24B detects that the reservoir 1B is empty the diffuser system 100B will enter a timeout state until the reservoir 1B is replenished. The diffuser system 100B can be adapted to notify the user to refill the reservoir 1B when the diffuser system 100B detects that the water level in the reservoir 1B is low.

The diffuser system can include a discharge liquid sensor 24B. In the illustrated embodiment, the discharge liquid sensor 24B is positioned on an inside surface of the discharge tray 4B and longitudinally aligned with a longitudinal axis of the substantially cylindrical discharge tray 4B. The discharge liquid sensor 24B can detect the presence of a liquid in the discharge tray 4B, such as, for example, through a change in the resistivity of the discharge liquid sensor 24B. The discharge liquid sensor 24B can communicate the reading of the discharge liquid sensor 24B to a central processing unit (CPU) or memory device of the diffuser system 100B. In some arrangements, if the discharge liquid sensor 24B detects that the discharge tray 4B is full the diffuser system 100B will enter a timeout state until the discharge tray 4B is emptied.

The diffuser system 100B can include a processor in the form of a computer chip 25B. The computer chip 25B can send and receive signals from the sensors connected to the computer chip 25B. For example, the computer chip 25B can receive a signal from the port valve ISB informing the computer chip 25B of the status of the port valve ISB, such as, for example, whether a container 12B is attached to the port valve ISB and the contents of the container 12B attached to the port valve ISB. The computer chip 25B can receive a signal from the discharge valve 21B informing the computer chip 25B whether the discharge valve 21B is opened or closed. The computer chip 25B can send a signal to the discharge valve 21B or the reservoir valve 16B to control operation of the valve. The computer chip 25B can receive a signal from the reservoir liquid sensor 23B or the discharge liquid sensor 24B. The computer chip 25B can be programmed to have fail-safe mechanisms, such as, for example, preventing the discharge valve 21B from opening or operating when the discharge liquid sensor 24B indicates the discharge tray 4B is full. The computer chip 25B can have wireless communication capability, such as WI-FI® capability, allowing the computer chip 25B to communicate with the sensors and valves wirelessly. In some configurations, the computer chip 25B communicates with the components of the diffuser system 100B through wired connections.

The processor which can be in the form of a computer chip 25B can include a wireless receiver or other similar component adapted for receiving commands sent from the API or from the network on which the diffuser system 100B is connected. The computer chip 25B can be listening for API commands sent from the network on which the diffuser system 100B is connected. The computer chip 25B can include a transmitter for transmitting information to the API or to the network on which the diffuser system is connected. As discussed in more detail below, the computer chip 25B can post status and data about its current functioning state to the API or to the network on which the diffuser system 100B is connected.

The diffuser system 100B can include a fan 26B. The fan 26B can be adapted to help force the atomized vapor through the duct 40B. The fan 26B can be a mini quiet fan. The fan 26B can be arranged to cool the computer chip 25B. In the illustrated embodiment, the fan 26B is positioned below the computer chip 25B to force air over the computer chip 25B and thereby cool the computer chip 25B. The fan 26B and the computer chip 25B can be positioned in a controller housing 31B that is below the atomizing chamber 3B. The diffuser system 100B can include venting ducts that communicate between the controller housing 31B and the atomizing chamber 3B. The venting ducts can enter the atomizing chamber 3B above the level of liquid within the atomizing chamber 3B, thereby allowing the airflow from the fan 26B to reach the duct 40B while preventing the liquid within the atomizing chamber 3B from draining into the controller housing 31B.

The diffuser system 100 can include a vaporizer 30B similar to the vaporizer except as described differently below. The vaporizer 30B can be an ultrasound liquid atomizer that can atomize a water solution. In the illustrated embodiment, the vaporizer 30B is positioned at the bottom of the atomizing chamber 3B. The atomizing chamber 3B can be adapted to receive water from the reservoir 1B and concentrate liquid 20 from the container 12. The atomizing chamber 3B can be adapted to convey the water and concentrate liquid 20 mixture to the vaporizer 30B. In some configurations, the bottom surface of the atomizing chamber 3B is sloped to convey the mixture of water and concentrate liquid 20 to the vaporizer 30B.

Figure 4:
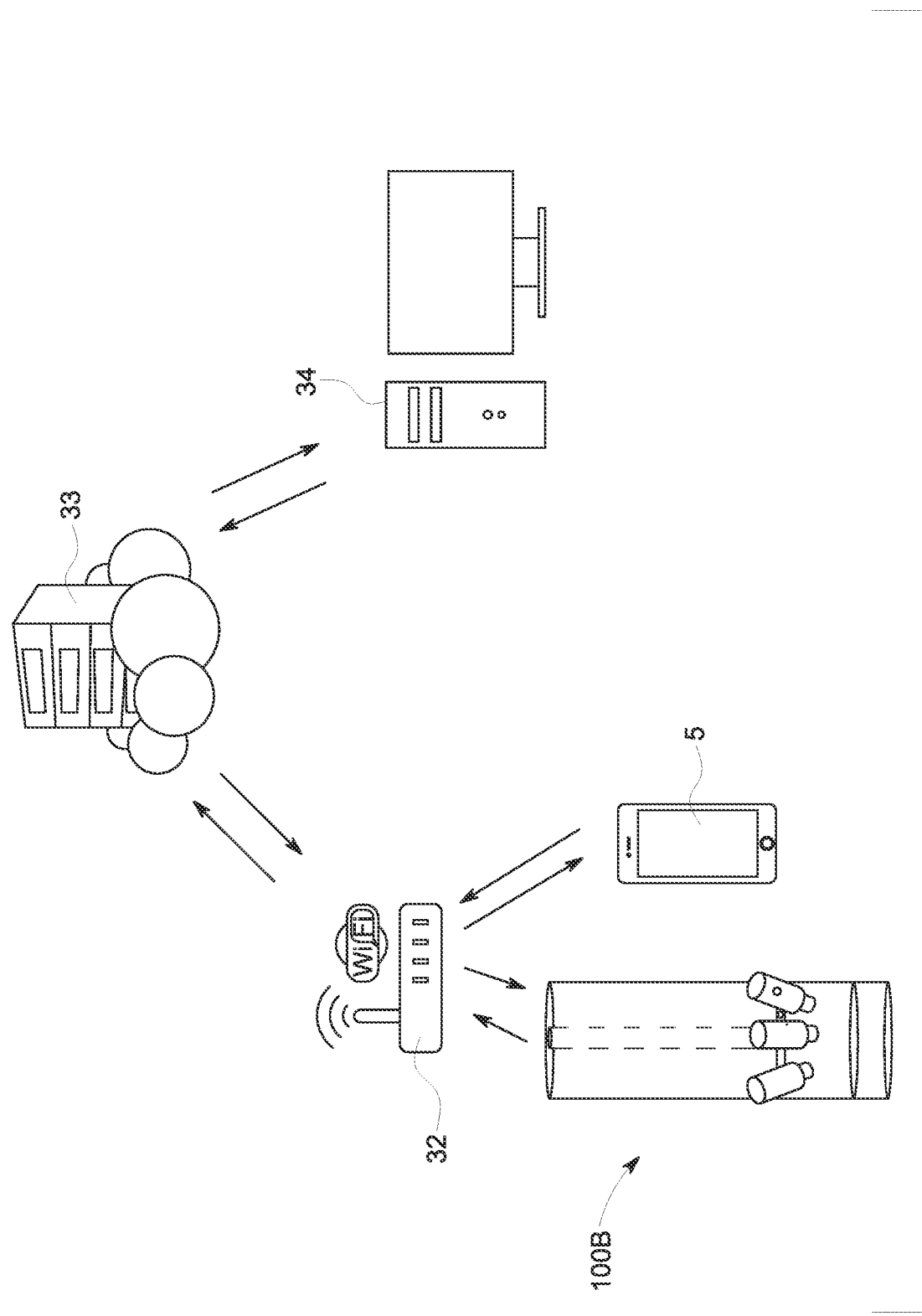
FIG. 4 IS a schematic diagram of an essential oil diffuser communicating with other electronic devices.

FIG. 4 is a schematic representation of how data will flow from a content management system (CMS) down to a user of the diffuser system 100B. As discussed above, the diffuser system 100B can include a wireless transmitter and receiver that allows the diffuser system 100B to communicate with a WI-FI® modem 32. The diffuser system 100B can communicate with a mobile device 5 directly or through an intermediary WI-FI® modem 32. The WI-FI® modem 32 can allow the diffuser system 100B to transmit and receive signals over the internet with a cloud server 33. The cloud server 33 can act as an intermediary between the diffuser system 100B and the CMS web application 34 that is used for maintaining the API.

Figure 5:
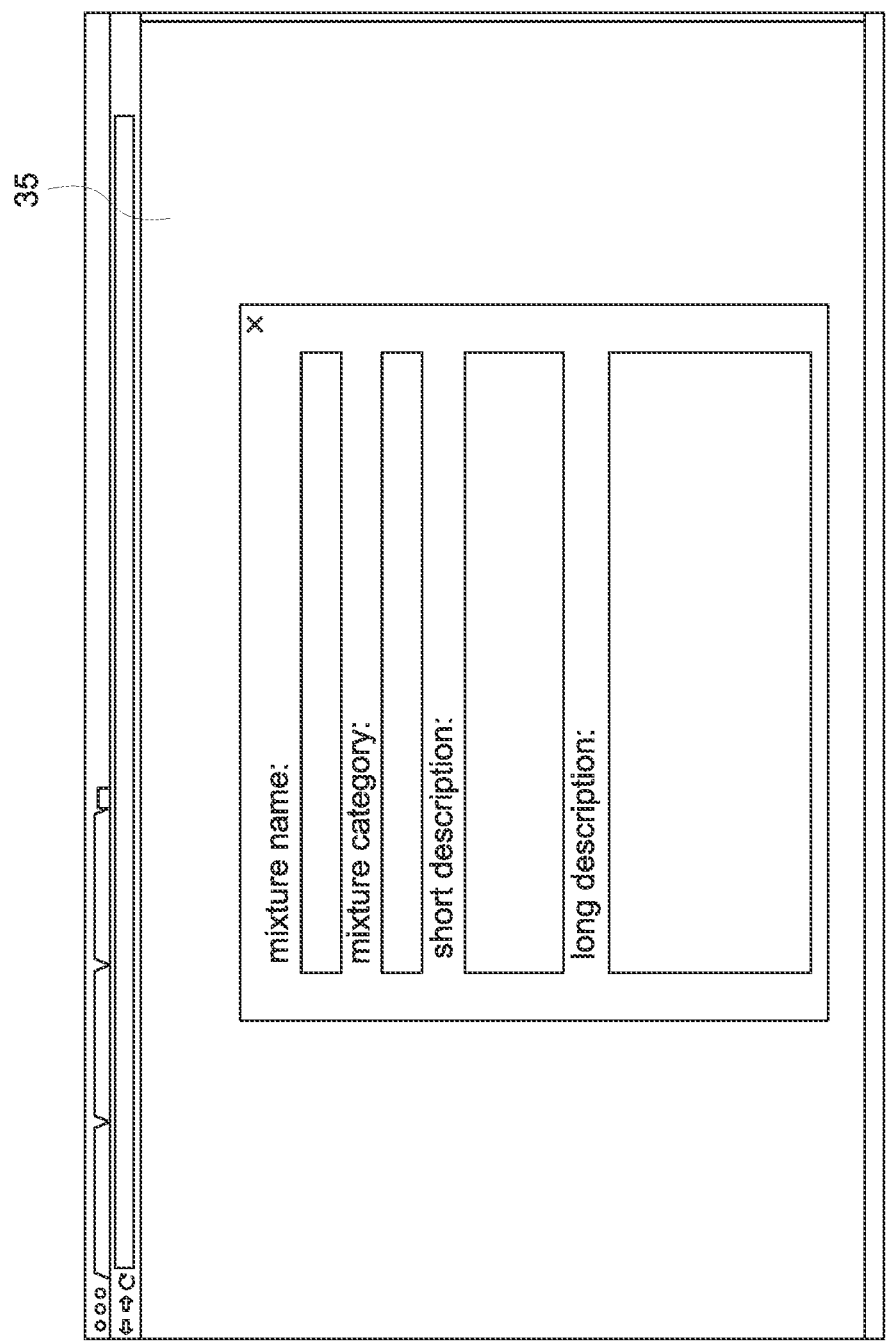
FIG. 5 shows an embodiment of a content management system associated with the essential oil diffuser of the present disclosure.

FIG. 5 represents a display rendering 35 of a CMS web application. The CMS web application can be maintained by the diffuser company. The CMS can control the available mixture categories with educational information and manage the ecommerce section of the mobile application. The CMS can save data to an API database. The mobile application can retrieve the data saved by the CMS to the API database.

Figure 6A:
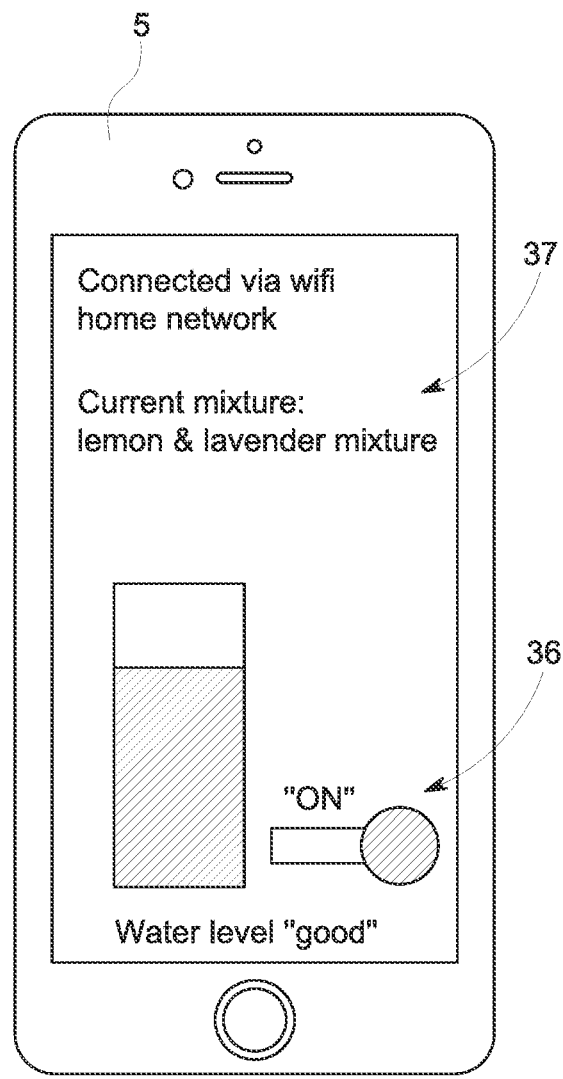
FIG. 6A shows a display of a mobile device running an embodiment of a mobile application for monitoring or controlling the essential oil diffuser of the present disclosure.
Figure 6B:
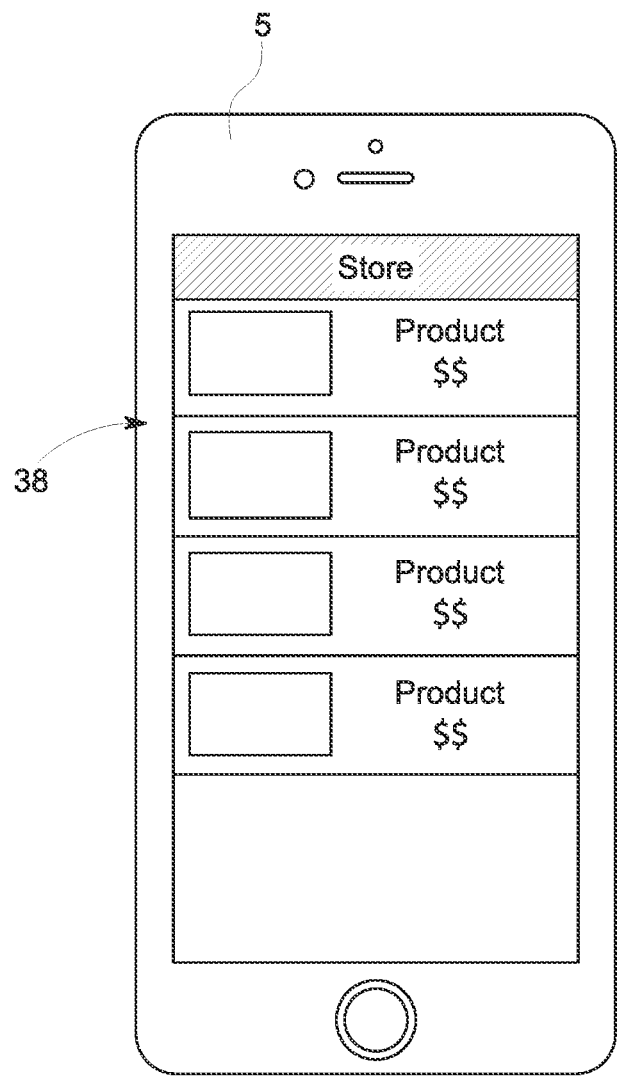
FIG. 6B shows a display of a mobile device running an embodiment of a mobile application for monitoring or controlling the essential oil diffuser of the present disclosure.
Figure 6C:
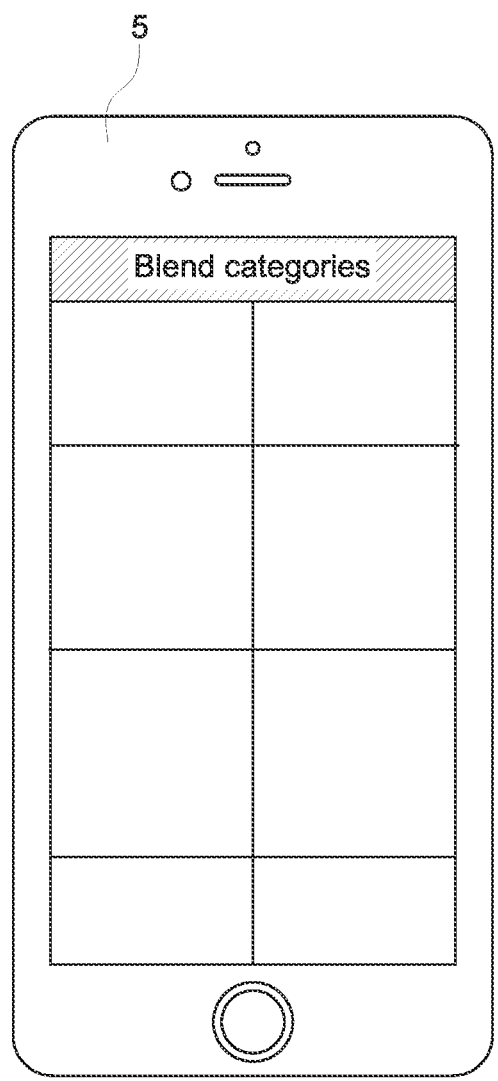
FIG. 6C shows a display of a mobile device running an embodiment of a mobile application for monitoring or controlling the essential oil diffuser of the present disclosure.

FIGS. 6A-6C show different illustrative displays of the mobile application of the diffuser system 100 operating on a mobile device 5. FIG. 6A shows a non-limiting display for controlling the diffuser system 100. The mobile application can display one or more icons 36 or text strings 37 to indicate the status of the diffuser system. The mobile application can keep track of the liquid levels in the diffuser system 100. For example, the mobile application can display on the mobile device 5 an icon 36 that indicates the level of the water in the reservoir 1B. The mobile application can inform the user of the liquid levels in the discharge tray 4B and the on/off state and colors of the LEDs of the light source 6B.

In some embodiments, the mobile application can track and/or store data. Such data can include, for example, the time of day the user uses the system, which blend is being used, and the like. The data can further include data polled from the user. For example, the mobile application can ask the user their stress level before starting the device and after using the device or for a general reason for operating the device. Such tracked and/or collected data may be used in machine learning algorithms to better understands the use habits of the consumer, provide suggestions of timing, blends, or the like, to the user based on the user responses and/or based on responses pooled from a plurality of like users.

In some embodiments, the mobile application can interact with a virtual reality system, where the device can automatically adjust a fragrance to match the virtual reality being seen by the user. For example, if the virtual reality displays a forest scene, a pine scent may be used in the device to match the virtual reality display.

FIG. 6B shows that the mobile application can display an interactive menu 38 that allows the mobile application to sell essential oils or related products directly to the user. If the user would like to create a mixture and they do not have the necessary oils, the app can "up sale" the oils directly to the user.

FIG. 6C shows that the mobile application can display different blend categories available to the user depending on which essential oil containers 12 are connected to the diffuser system 100. A chosen mixture can be represented in the app with an image that represents the blend category, a combination of essential oils, and an LED hue that will illuminate through the water reservoir 1B while the blend is atomized by the diffuser system 100.

FIG. 7 shows a discharge valve 18C, also referred to herein as a drop control mechanism 18C, that can digitally control the flow of a concentrate liquid 20 to be mixed into a volume of water from the water reservoir, as described previously. The drop control mechanism 18C can be attached to the diffuser system 100 that will atomize a combination of water and the contents of a container 12 inserted into the drop control mechanism 18C. The drop control mechanism 18C can dispense essential oils, chemicals, or medicine. The drop control mechanism 18C can produce drops 44 that are measured in microliters for the medical industry. The drop control mechanism 18C can include a piezoelectric element adapted to create pulses in order to control drop size and/or frequency. The drops 44 can be dispensed from a drip dispenser tip 46. A digital solenoid or digital flow control valve 48 can regulate the drop 44 volume. The drop control mechanism 18C can have an input slot 50 that receives the container 12 that contains the liquid concentrate 20. The drop control mechanism 18C can include a motor, a solenoid valve, a piezo valve, or a pump. The diffuser system 100 can be adapted to prevent or reduce clogging of the pump internals with such materials as, for example, essential oils that have been exposed to air. As the essential oils travel through the internals of the pump, the essential oils could clog flow through the internal flow systems of the pump diffuser after being exposed to air. The diffuser system 100 can include a pump mechanism (e.g., a dual tube connection to the pump) that pulls in the essential oil and water at the same time. Pulling essential oil and water into the pump at the same time can dilute the essential oil with water and reduce the viscosity of the liquid flowing through the pump. Mixing the essential oil with water upon drawing the essential oil into the pump can limit the contact of essential oils with the pump internals. The pump internals are exposed to a diluted essential oil that is less likely to clog the pump due to its mixture with water.

Figure 8A:
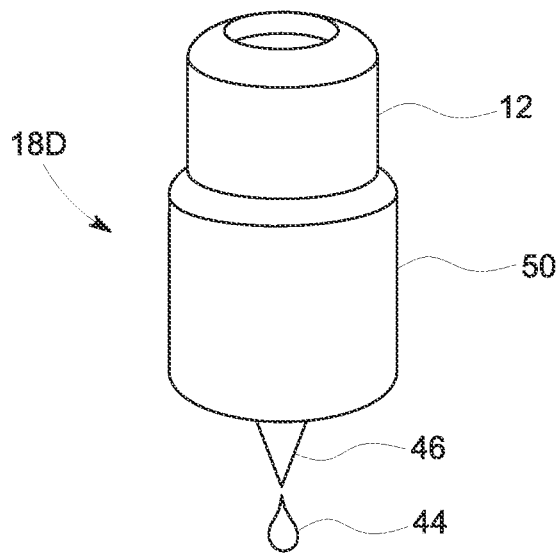
FIG. 8A shows an embodiment of a drop control mechanism with a drip dispenser at the bottom of the drop control mechanism.
Figure 8B:
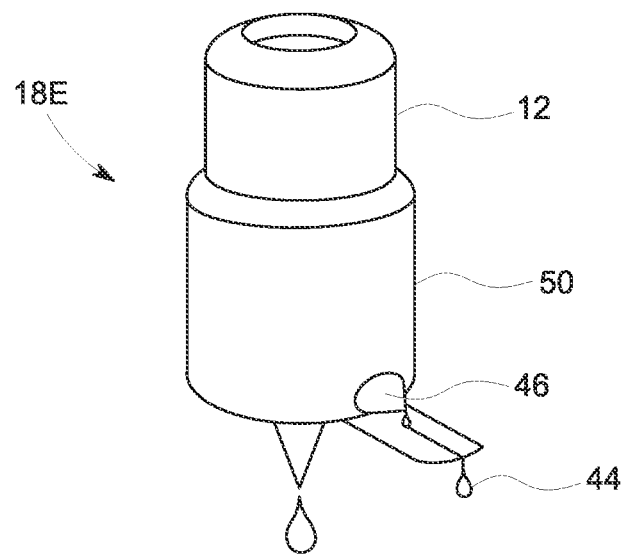
FIG. 8B shows an embodiment of a drop control mechanism with a drip dispenser at the side of the drop control mechanism.

FIGS. 8A and 8B show embodiments of a drop control mechanism 18D, 18E with a container 12 inserted into the input slot 50 of the drop control mechanism 18D, 18E. FIG. 8A shows a drop control mechanism 18D in which the output dispenser tip 46 is placed on the bottom of the mechanism. FIG. 8B shows a drop control mechanism 18E in which the output dispenser tip 46 is placed on the side of the drop control mechanism 18E.

Figure 9:
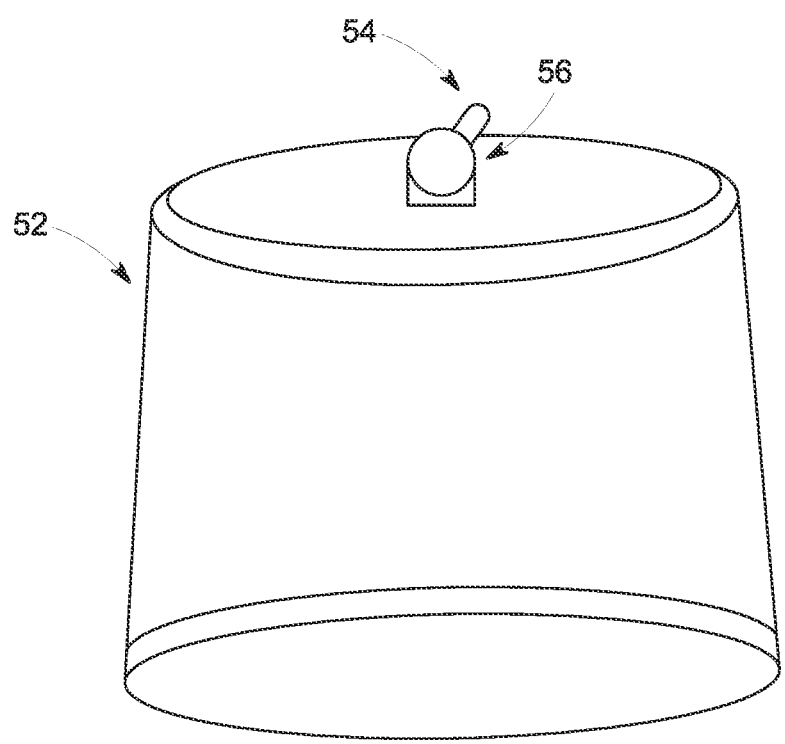
FIG. 9 shows an embodiment of a removable upper cover associated with the essential oil diffuser system of the present disclosure.

FIG. 9 shows a removable upper cover 52 of a diffuser system 100. The upper cover 52 can contain an output nozzle 54 that is attached to a ball pivot joint 56 to adjust the direction of the atomized mist output. The output nozzle 54 can also function as an adapter where medical grade tubing can be attached for inhalation through the mouth or nose or both (see, e.g., FIG. 12). The output nozzle 54 can also function as an adapter where tubing can be attached to direct the output onto a user's skin (e.g., transdermal application).

Figure 10:
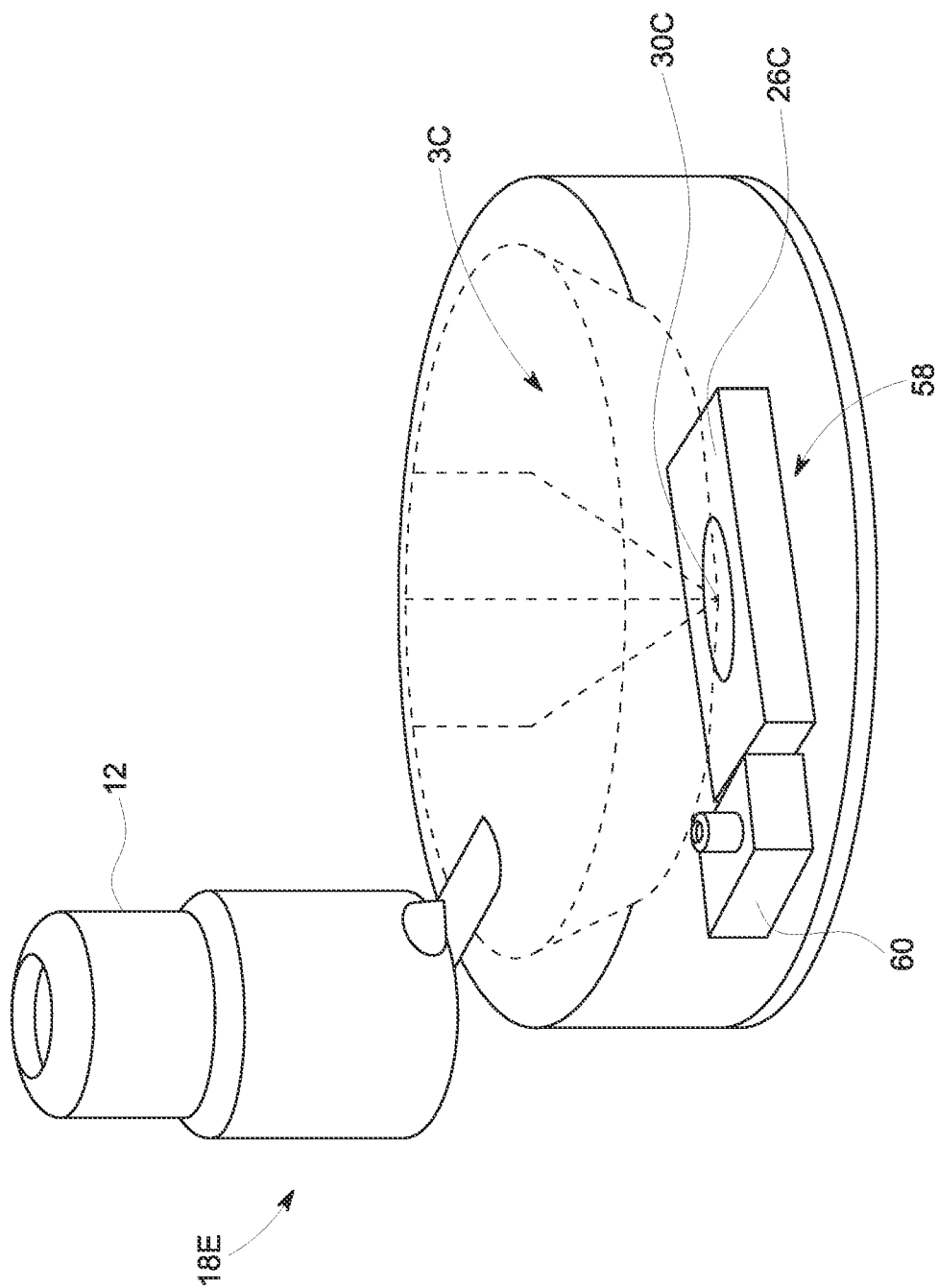
FIG. 10 shows an embodiment an atomization chamber associated with the essential oil diffuser system of the present disclosure.

FIG. 10 shows a bottom portion of a diffuser device that contains an atomization chamber 3C, a drop control mechanism 18E, a computer chip 58, and a fan 26C. The drop control mechanism 18E can be positioned so that the output liquid will be directed into the atomization chamber 3C to be mixed with water. The diffuser system 100 can include a vaporizer 30C (e.g., ultrasonic atomizer module) that vaporizes the liquid mixture comprising water and concentrate liquid (e.g., essential oil). The diffuser system 100 can contain one or more drop control mechanisms 18E. The diffuser system 100 can have a pump 60 that is attached to each drop control mechanism 18E to create pressure to help create a more accurate sized drop. The diffuser system 100 can have a computer chip 58 to control the mechanisms (e.g., pump 60) within the diffuser. The diffuser system 100 can be controlled by an onboard touch screen, mobile application, or onboard buttons.

Figure 11:
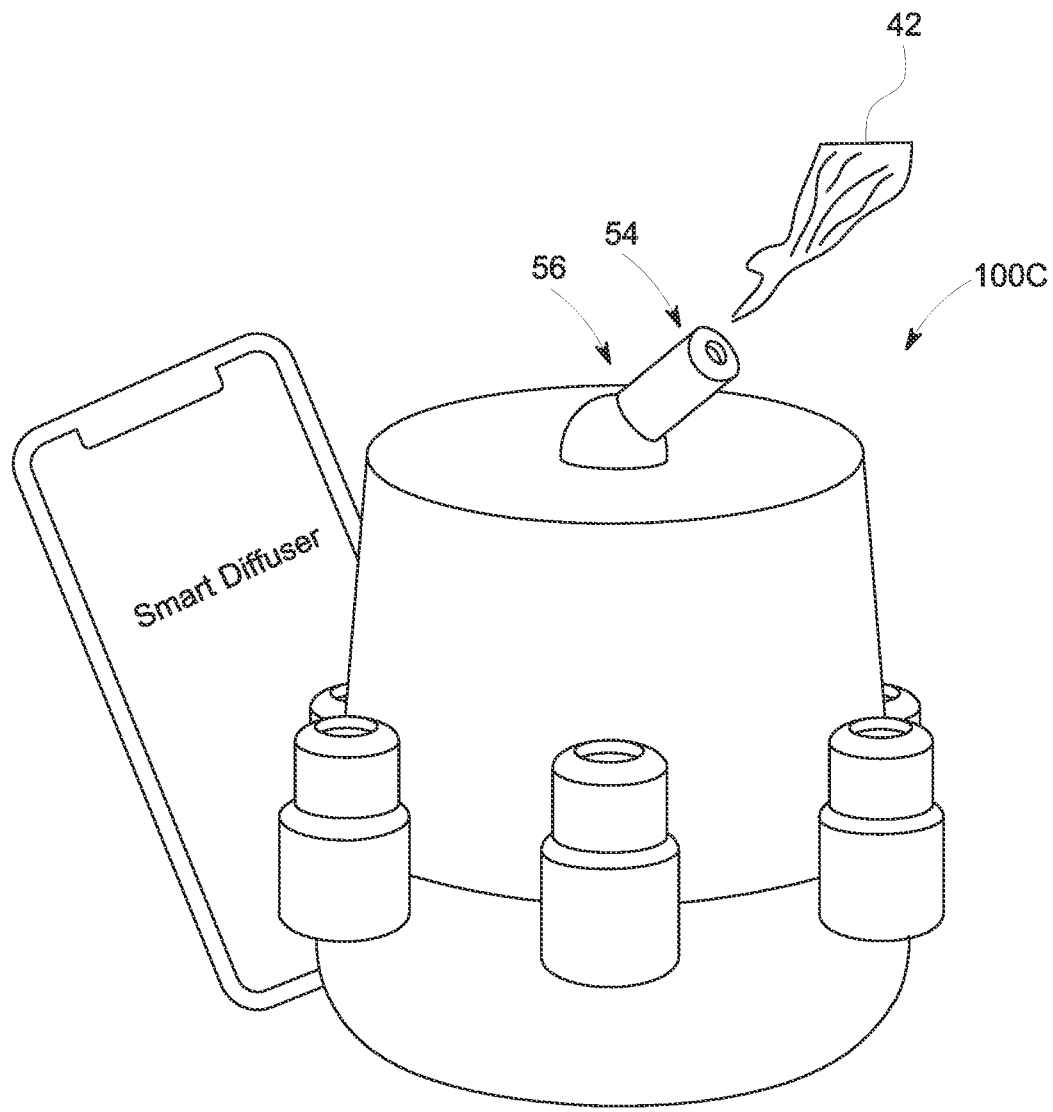
FIG. 11 shows an embodiment the essential oil diffuser system of the present disclosure having an articulating outflow nozzle.

FIG. 11 shows a diffuser system 100C with a ball pivot joint 56 to adjust the direction of the output nozzle 54, thereby allowing a user to direct the outflow path of the mist 42 produced by the diffuser system 100C.

Figure 12:
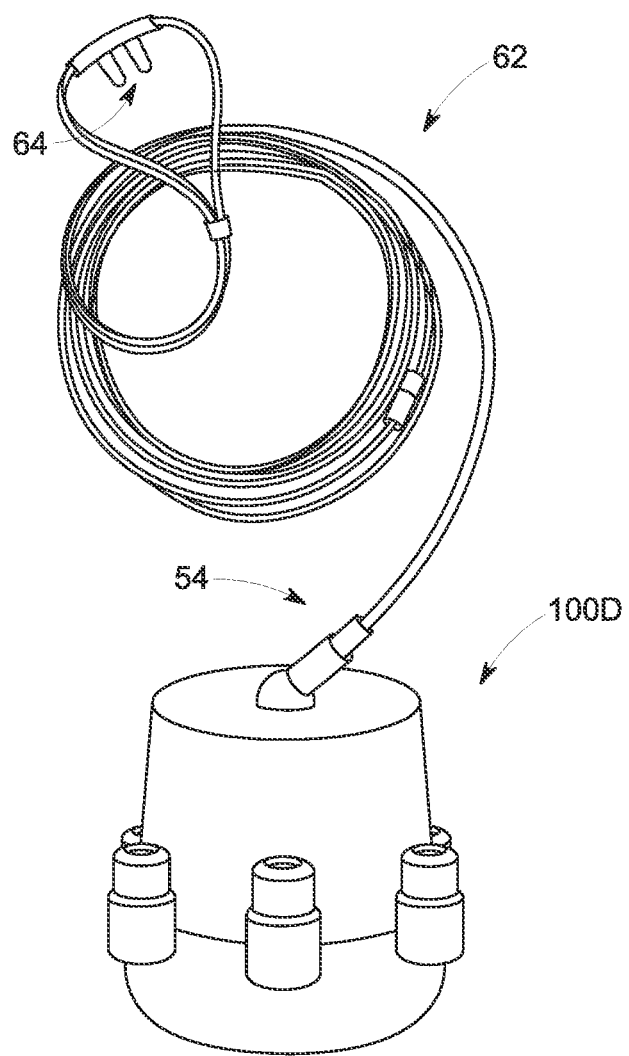
FIG. 12 shows an embodiment of the essential oil diffuser system of the present disclosure having a nasal cannula attached to an outflow nozzle of the diffuser.

FIG. 12 shows a diffuser system 100D with a nasal cannula 62 attached to the output nozzle 54 of the diffuser system 100D. The nasal cannula 62 can include a pair of prongs 64 that guide the mist 42 from the diffuser 100D into the nostrils of a user. In some embodiments, an inhalation mask (not shown) or other face-mask-type breathing interface can be attached to the output nozzle 54 so that the user can inhale the emitted mist using a breathing interface that does not have prongs extending into the nostrils of the user. The aforementioned diffuser systems 100, 100A, 100B, 100C, 100D can be used at the consumer level, business level (e.g., waiting rooms, commercial establishments), or medical level (e.g., hospital, psychiatrist office). A consumer-level diffuser system can have components with tolerances that are different from a medical-level diffuser system. For example, a consumer-level diffuser system may have a less precise drop control mechanism 18C compared to a medical-level diffuser system, thereby allowing the consumer-level diffuser system to have a lower price compared to the medical-level diffuser system.

Figure 13A:
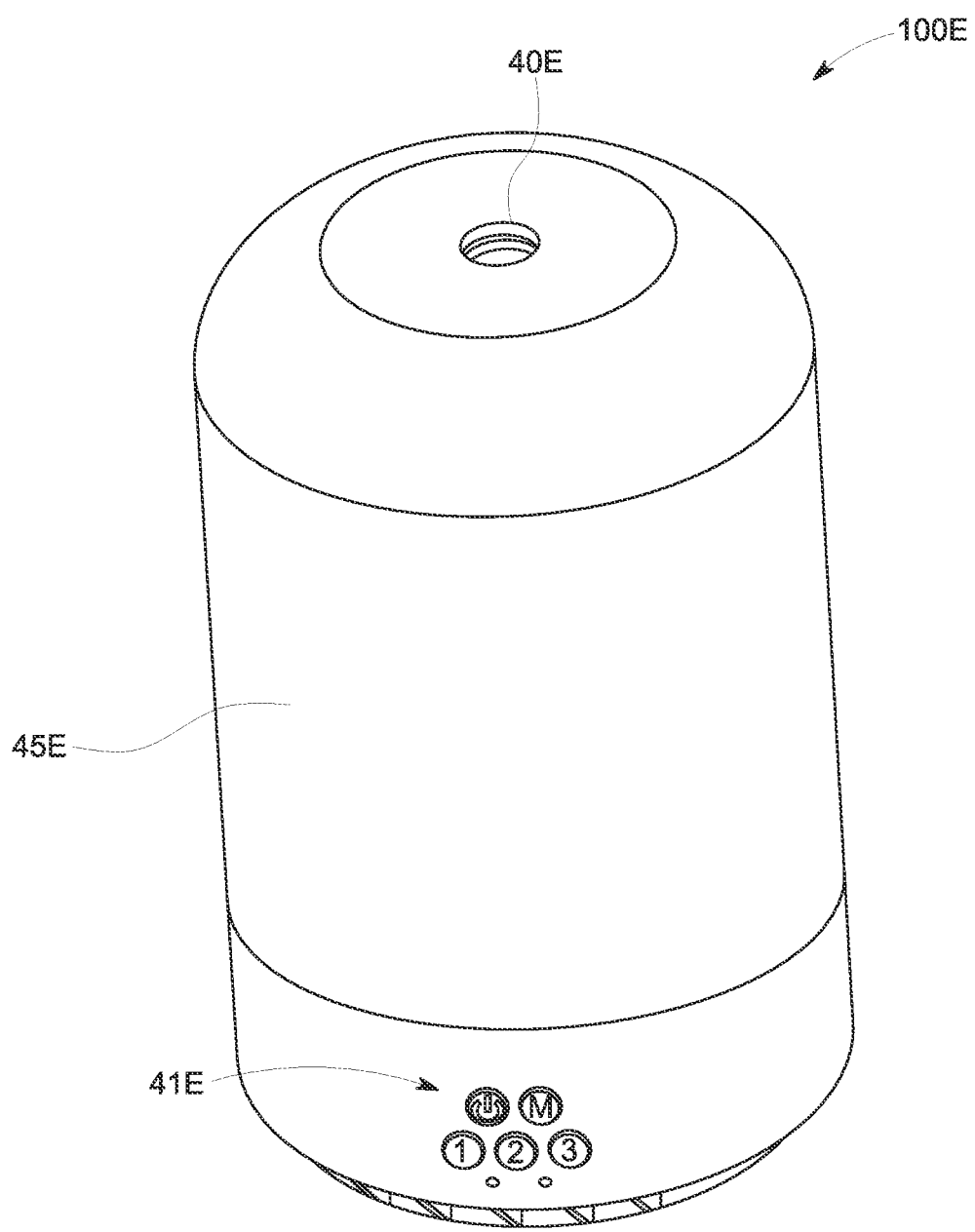
FIG. 13A shows a top perspective view of an embodiment of the essential oil diffuser system of the present disclosure.

FIG. 13A illustrates another embodiment of a diffuser system 100E similar to the diffuser system 100 except as described differently below. The features of the diffuser system 100E can be combined or included with the diffuser system 100 or any other embodiment discussed herein. The diffuser system 100E can have a central duct 40E through which the diffuser system 100E emits a vapor (e.g., a mist of nebulized or atomized liquid), as described above with regard to the central duct 40A of the diffuser system 100A shown in FIG. 2. The diffuser system 100E can include a number of interface buttons 41E. The interface buttons 41E can include one or more of a power button, a memory program button, a memory recall button and/or a concentrate liquid dispensing button for dispensing a predetermined amount of concentrate liquid into the reservoir and/or vaporization chamber. As described below, the diffuser system 100E can include a plurality of bottles of essential oils (e.g., three bottles of different essential oils) that are positioned within the housing 45E of the diffuser system 100E. The diffuser system 100E can include a processor that allows the diffuser system 100E to be programmable with regard to the mixture of essential oils that are introduce into a foundation liquid that is then atomized (e.g., using ultrasonic atomization) by the diffuser system 100E.

In some embodiments, the concentrate liquid (such as the essential oil) may be dropped into the foundation liquid at a distribution location that is a distance above the top level of the liquid. In this embodiment, the drop control mechanism can operate in reverse to permit excess concentrate liquid to move back into their respective bottle, thus removing the excess contact of the concentrate liquid within the pump and/or lines between the concentrate liquid bottles and its distribution location.

Figure 13B:
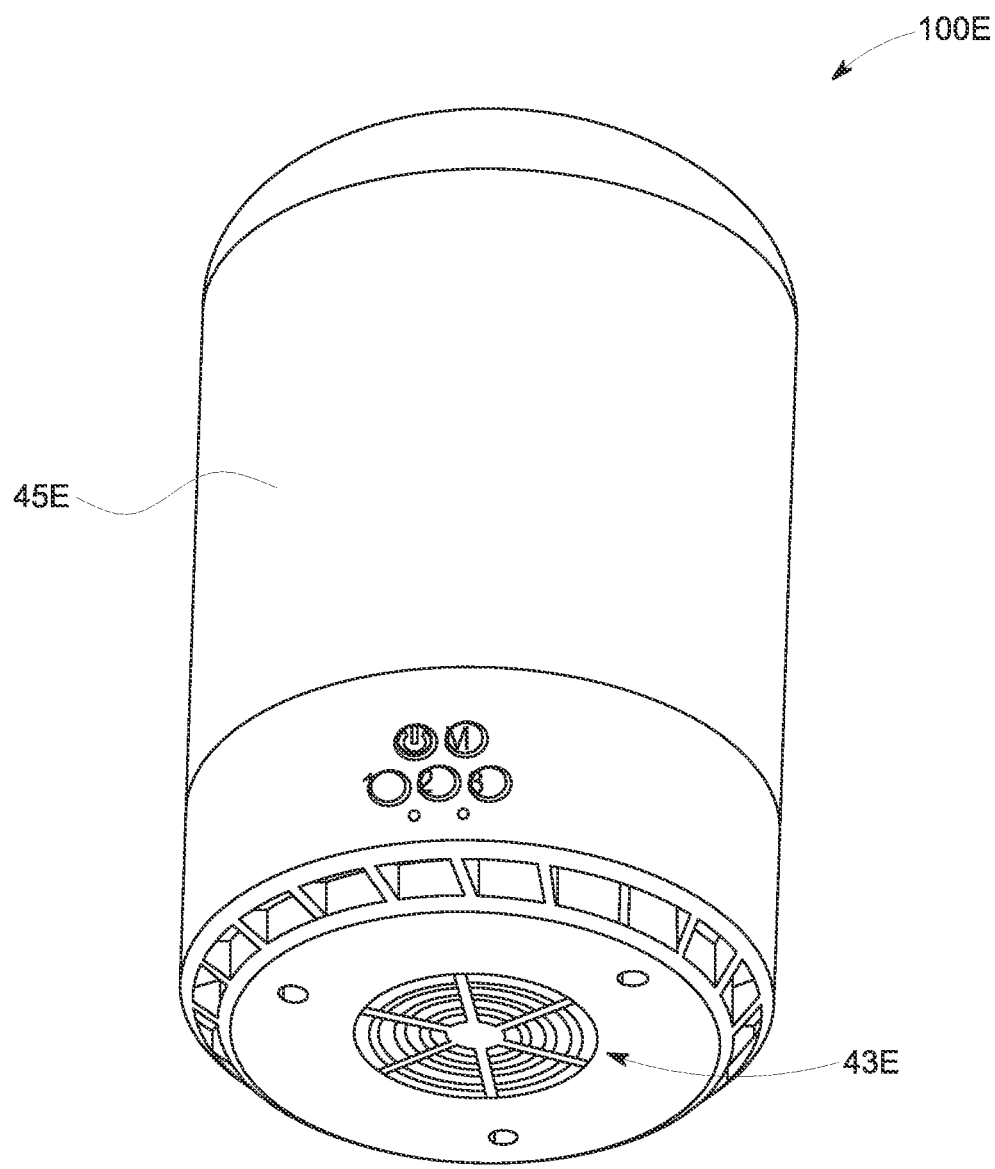
FIG. 13B shows a bottom perspective view of the essential oil diffuser system of FIG. 13A.

FIG. 13B shows the bottom of the diffuser system 100E can include an air intake 43E. The air intake 43E can provide a flow path for air to enter the housing and enter the fan that is disposed within the housing of the diffuser system 100E. As discussed above with regard to FIG. 3, the diffuser system 100E can include a fan that enhances the delivery of the vapor from the duct 41E of the diffuser system 100E.

Figure 14:
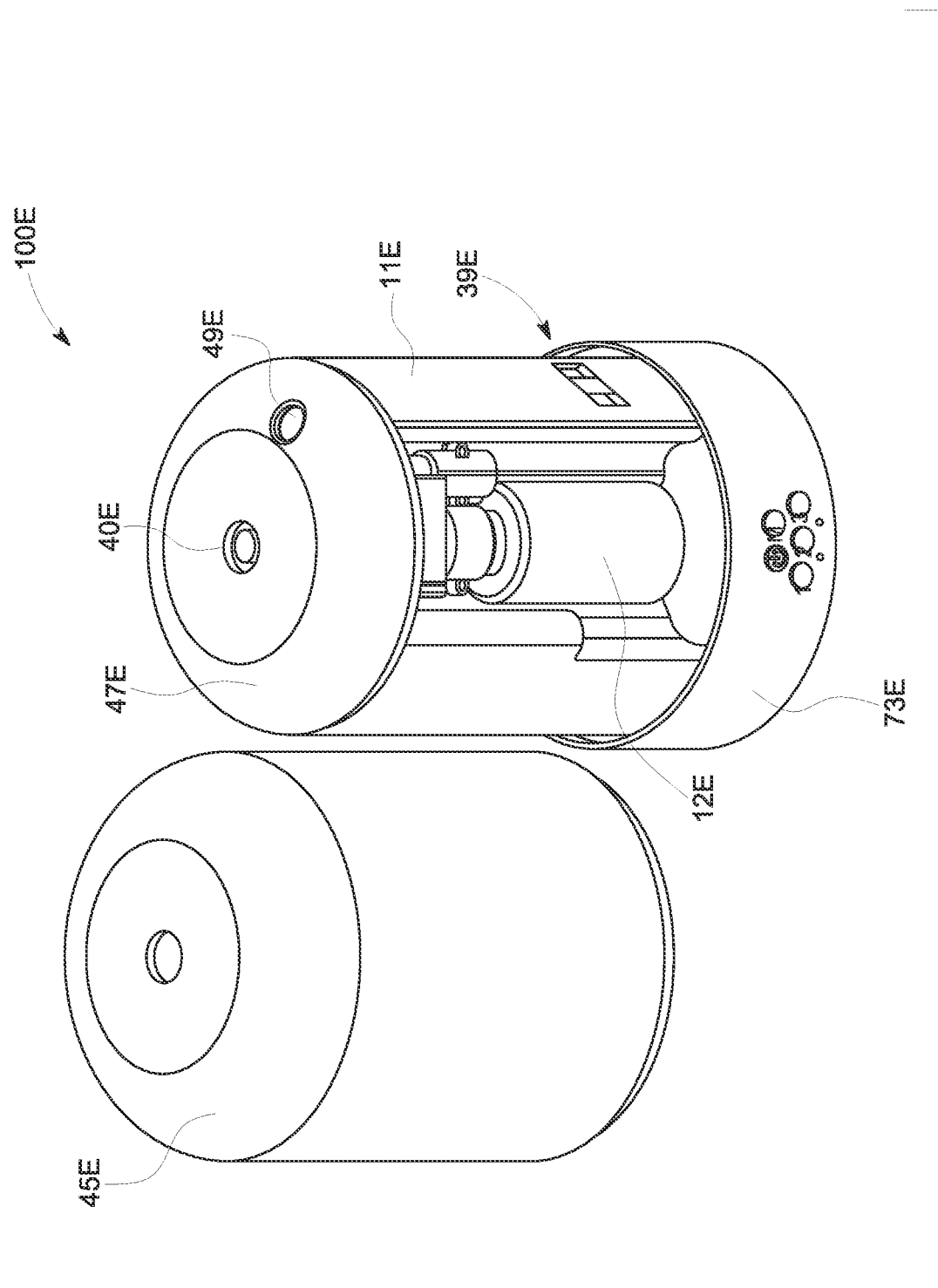
FIG. 14 shows a top perspective view of the essential oil diffuser system of FIG. 13A with the top cover removed.

FIG. 14 shows the diffuser system 100E with the outer housing 45E removed to show the internal components of the diffuser system 100E. In the illustrated embodiment, the diffuser system 100E is configured to hold three containers 12E. As discussed, the containers 12E can hold a liquid such as an essential oil. The diffuser system 100E can have a reservoir cap 47E. In the illustrated embodiment, the reservoir cap 47E has a fill port 49E that allows a user to fill the reservoir without removing the reservoir cap 47E. The reservoir cap 47E can also include a central opening that provides a flow path for the duct 40E to allow nebulized vapor to exit the housing of the diffuser system 100E. The diffuser system 100E can include an air outlet 39E that is disposed at the side of the inner structure 11E, as shown in FIG. 14. The air outlet 39E allows the air to flow from the base 73E of the diffuser system 100E, where the fan is located, into the space between the inner structure 11E and the outer shell 45E, which forces the atomized vapor out of the diffuser system 100E.

Figure 15:
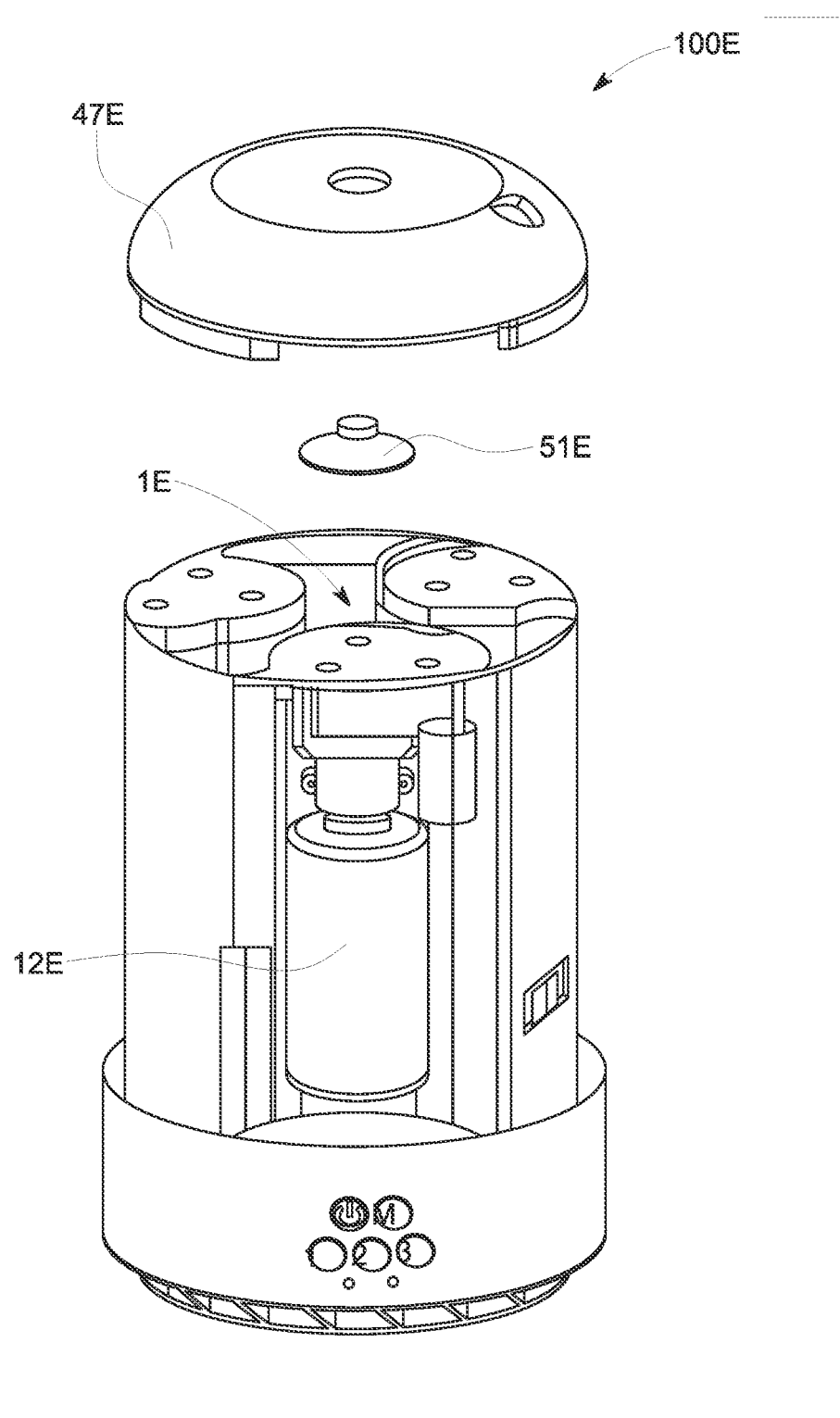
FIG. 15 shows a side perspective view of the internal components of the essential oil diffuser system of FIG. 13A.
Figure 16:
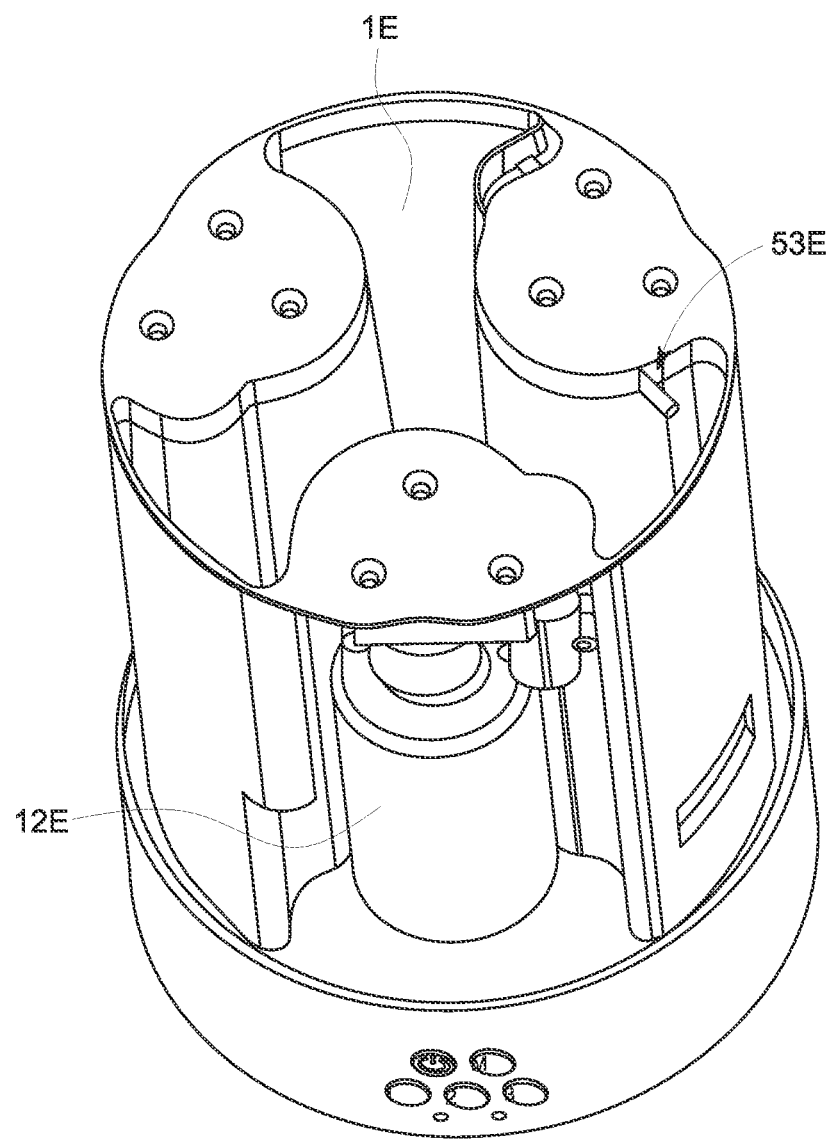
FIG. 16 shows a top view of internal space of the reservoir of the essential oil diffuser system of FIG. 13A.
Figure 17:
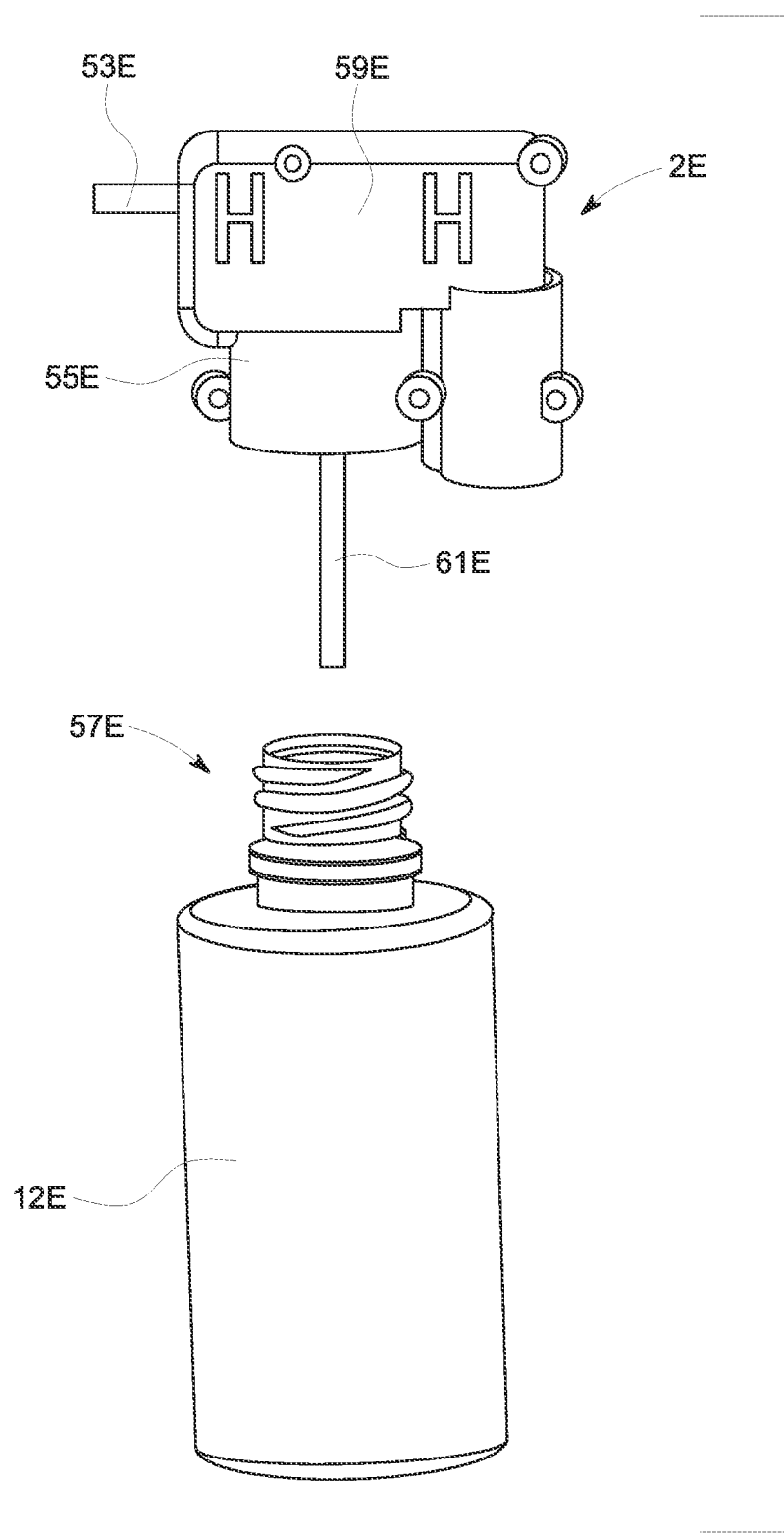
FIG. 17 shows an assembly view of a docking station and container of the essential oil diffuser system of FIG. 13A.

FIG. 15 shows the diffuser system 100E with the reservoir lid 47E removed to show the internal space of the reservoir 1E. In some embodiments, the diffuser system 100E can include a shade 51E that is disposed near the central opening of the reservoir lid 47E and between the reservoir lid 47E and the reservoir 1E. The shade 51E can be arranged so that it blocks a vertical line of sight into the interior space of the reservoir 1E through the central opening of the reservoir lid 47E. A foundation liquid (e.g., water) can be placed in the reservoir 1E. As discussed further below, the diffuser system 100E can add to the foundation liquid that is within the reservoir 1E drops of the essential oils from the containers 12E that are installed in the diffuser system 100E. The addition of the drops can be according to a recipe that mixes a first volume of one type of essential oil with a second volume of another type of essential oil. The first and second volumes may be equal or different. The recipe can be pre-programmed into the diffuser system 100E.

FIG. 16 is a partial top view of the internal space of the reservoir 1E. The drops of the liquid from the container 12E can enter the liquid within the reservoir 1E by dropping into the liquid from a spout 53E. In the illustrated embodiment, the spout 53E for each container 12E is disposed near the top of the reservoir 1E. In some arrangements, the spout 53E is positioned to enhance dispersion of the oil droplet into the foundation liquid. In the illustrated embodiment, the spout 53E is placed near the top of the reservoir 1E to increase the impact of the oil droplet on the surface of the foundation liquid.

FIG. 17 shows a container 12E and the docking station 2E. As discussed above, the docking station 2E is configured to receive a container 12E of liquid (e.g., essential oil). The docking station 2E can have a collar 55E with an internal thread that mates with an external thread 57E on the mouth of the container 12E, as shown in FIG. 17. The docking station 2E can have a housing 59E that is adapted to anchor the docking station 2E to the outer surface of the reservoir 1E. The docking station 2E can include an intake tube 61E that extends into the container 12E when the container 12E is installed onto the docking station 2E, for example by mating the external thread 57E on the container 12E with the internal thread on the collar 55E of the docking station 2E. As shown in FIG. 16, the diffuser system 100E can include three docking stations 2E that are each configured to receive a container 12E. As described in more detail below, each of the docking stations 2E can deliver to the foundation liquid in the reservoir 1E a droplet having a precise volume, allowing customization of the fragrance or therapeutic effect of the vapor emitted from the diffuser system 100E.

FIG. 18 shows an embodiment of a docking station 2E with the front of the docking station housing 59E removed to show the internal components of the docking station 2E. The docking station 2E can include a fluid delivery system that is capable of delivering precise droplet volumes. The droplet delivery system can include a motor 63E. The motor 63E can turn a drive gear 65E (e.g., worm gear). The drive gear 65E can mesh with a driven wheel 67E such that the motor 63E indirectly drives the driven wheel 67E through the drive gear 65E. Accordingly, the motor 63E can achieve precise rotation of the driven wheel 67E about the axis of the driven wheel 67E. As shown in FIG. 18, a tubing portion 69E can connect the intake tube 61E with the spout 53E. The tubing portion 69E can wrap around a periphery of the driven wheel 67E. The driven wheel 67E can have a cam surface that compresses the tubing portion 69E against a radially outward side wall. As the driven wheel 67E rotates, the cam surface squeezes the tubing near the intake tube 61E and rotates this squeezed point of contact on tubing around the axis of the driven wheel 67E toward the spout 53E, driving a volume of liquid in the tubing portion 69E and ahead of the squeezed point of contact toward the spout 53E. A droplet sensor 71E can be disposed at or near the spout 53E. The droplet sensor 71E can be arranged to detect the volume of liquid in droplet delivered through the spout 53E. In some embodiments, the droplet sensor 71E can be an infrared sensor. In certain variants, the droplet sensor 71E can have the functionality of detecting the amount of the essential oil that is output from the drop delivery system of the diffuser system 100E. The droplet sensor 71E can be configured to send a signal to the processor of the diffuser system 100E to inform the diffuser system 100E of the precise drop amount and also to calculate if the oil is running out and whether a new container 12E of the essential oil should be installed or ordered. The diffuser system 100E can include a droplet sensor 71E on each spout 53E of the diffuser system 100E. For example, in the illustrated embodiment, the diffuser system 100E would have three droplet sensors 71E, one for each spout 53E of the diffuser system. In some embodiments, where there is a single outlet spout for each of the plurality of bottles, there may be a single droplet sensor 71E on the single outlet spout.

In some embodiments, the droplet sensor 71E is installed hidden inside the spout 53E or plastic housing of the docking station 2E. The diffuser system 100E can include a capacitive sensor 94E. The capacitive sensor 94E can be adapted to inform the diffuser system 100E when a container 12E attached to the droplet delivery system is empty.

FIG. 19 shows an embodiment of a base 73E of the diffuser system 100E. The base 73E can include a cover 75E. The cover 75E can be adapted to connect with the reservoir 1E. In the illustrated embodiment, the cover 75E has a plurality of through holes 77E. The through holes 77E can be used to pass through fittings that secure the cover 75E to the reservoir 1E. At least one of the through holes 77E can be used to provide a flow path from the reservoir 1E to the atomization chamber 3E of the diffuser system 100E. The diffuser system 100E can include a light ring 76E. The light ring 76E can be adapted to illuminate the reservoir 1E or other portion of the diffuser system 100E. The light ring 76E can be a printed circuit board assembly (PCBA) with one or more light emitting diode (LED) lights disposed on the light ring 76E.

FIG. 20 is an exploded view of the base 73E shown in FIG. 19. The cover 75E can fit over the mouth of a bottom housing 79E to form an enclosed base housing that contains components of the diffuser system 100E. The base housing can house the fan 26E. As shown in FIG. 20, the cover 75E can have a central opening 81E. The fan 26E can be arranged to push air out of the housing of the base and through the central opening 81E. The diffuser system 100E can include a piezoelectric element 83E or other element adapted to atomize liquid, as discussed previously. In the illustrated embodiment, the piezoelectric element 83E is supported on an ultrasonic piezo base 85E. A sealing ring 87E can be disposed at the periphery of the ultrasonic element 83E. The sealing ring 87E can have a gate or channel 89E that controls access to the piezoelectric element 83E. The diffuser system 100E can be arranged so that liquid from the reservoir 1E must pass through the gate 89E to reach the piezoelectric element 83E. The gate 89E can include a valve that regulates whether liquid can flow through the gate 89E. The diffuser system 100E can include a processor that controls whether the valve of the gate 89E is in an open or closed configuration. The diffuser system 100E can include a keyboard 91E. The keyboard 91E can be adapted to send a signal to a processor to indicate which of the interface buttons 41E have been pressed.

Figure 21A:
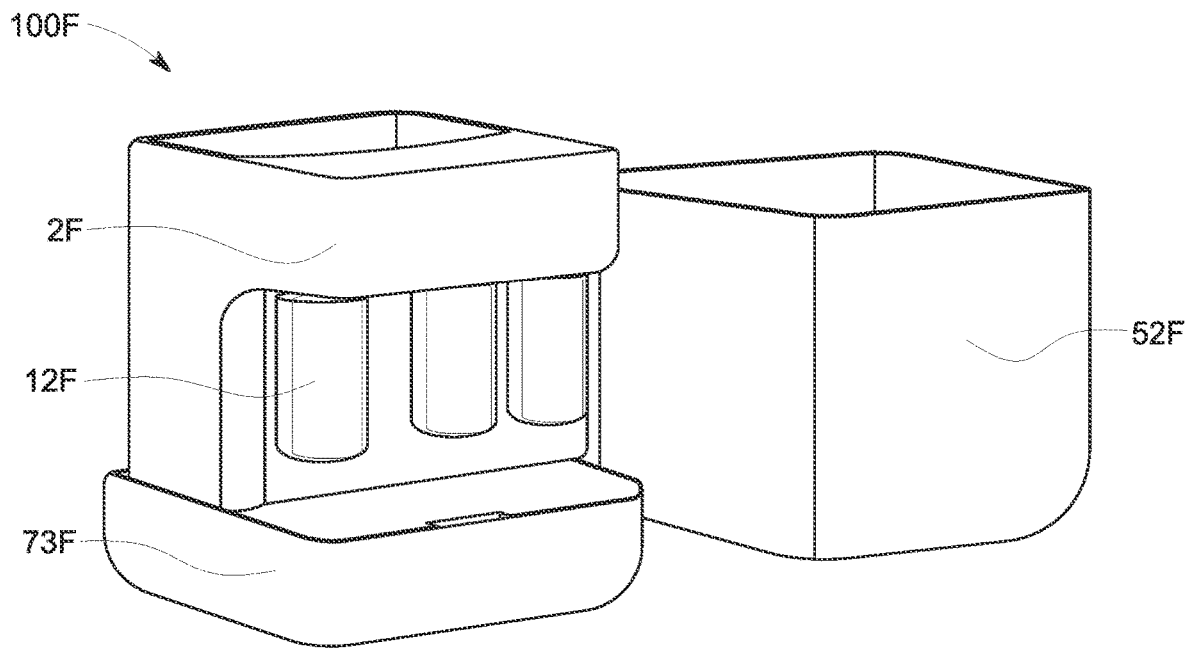
FIG. 21A shows a perspective view of an embodiment of the essential oil diffuser system of the present disclosure with a top cover removed from a base portion.

FIG. 21A illustrates another embodiment of a diffuser system 100F similar to the diffuser system 100 except as described differently below. The features of the diffuser system 100F can be combined or included with the diffuser system 100 or any other embodiment discussed herein. The diffuser system 100F can have a removable upper cover 52F that seats over top a base 73F. The base 73F can include a docking station 2F that receives one or more containers 12F of essential oil, as discussed herein.

Figure 21B:
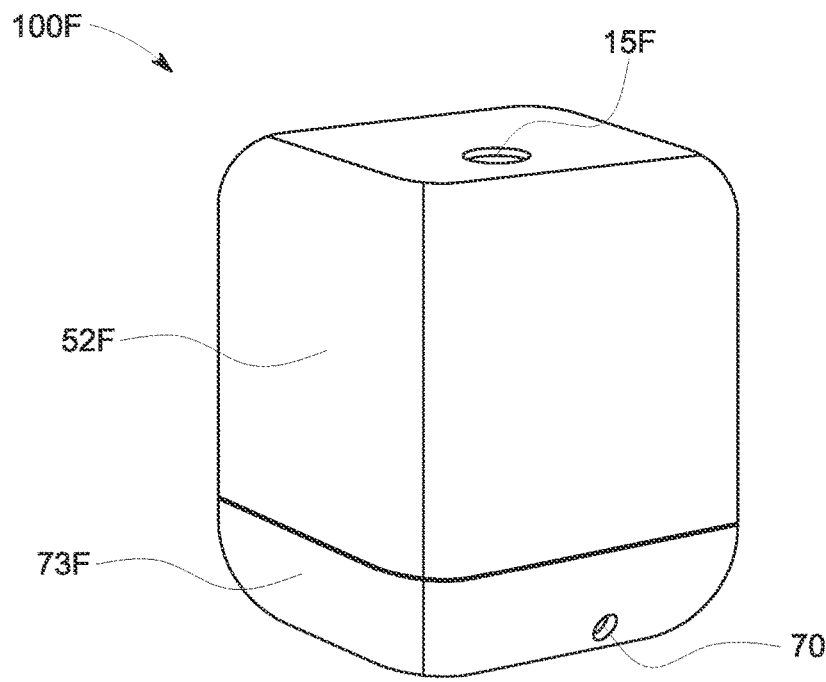
FIG. 21B shows a partial rear view of the essential oil diffuser system of FIG. 21A with the cover seated onto the base portion.
Figure 21C:
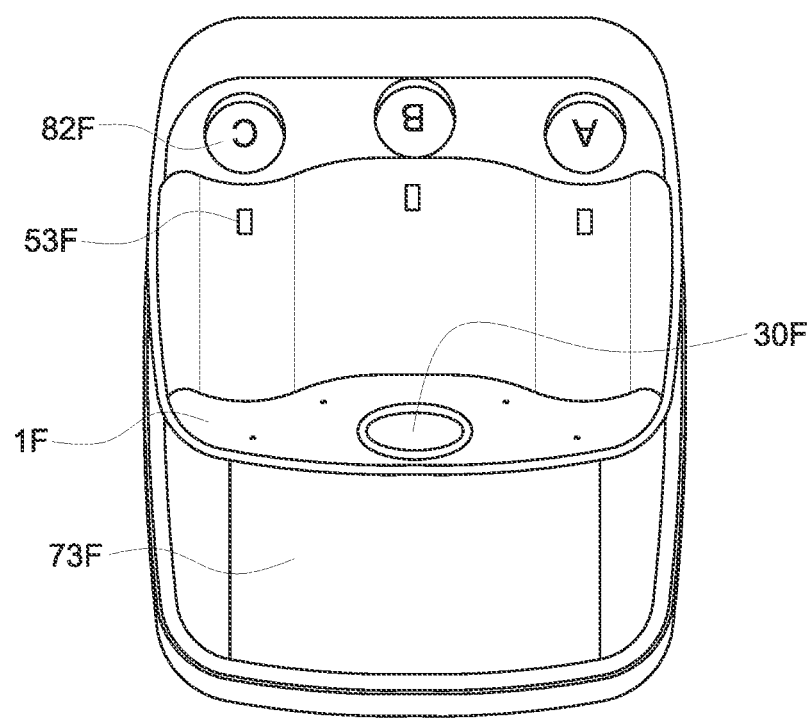
FIG. 21C shows a top view of the base portion of the essential oil diffuser system of FIG. 21A.

FIG. 21B shows the diffuser system 100F with the removable cover 52F seated on the base 73F. The removable cover 52F can include a central opening 15F through which mist or vapor 42 (FIG. 11) can be emitted from the diffuser system 100F. The diffuser system 100F can have a cuboidal shape when the removable cover 52F is seated on the base 73F. The diffuser system 100F can include a power jack 70. The power jack 70 can be disposed on the rear face of the base 73F.

FIG. 21e shows a top view of the base 73F. The base 73F can include one or more spouts 53F that extend into the reservoir 1F. The spouts 53F can be in fluid communication with the container 12F. The spout 53F can introduce essential oil from the container 12F into the foundation liquid (e.g., water) that is contained within the reservoir 1F, as discussed herein. The base 73F can include a container indicator 82F. The diffuser 100F can have a container indicator 82F corresponding to each container port of the docking station 2. The container indicator 82F can inform the user of the status of the container 12F associated with the container indicator 82F. The container indicator 82F can include a light source that illuminates or changes color to indicate the status of the container 12F associated with the container indicator 82F. The container indicator 82F can glow green when the container 12F associated with the container indicator 82F is full or more than half-full of essential oil. The container indicator 82F can glow red when the container 12F is empty. The container indicator 82F can glow white when no container 12F is attached to the corresponding connector port of the docking station 2F.

As shown in FIG. 21e, the diffuser system 100F can have a vaporizer 30F (e.g., a piezoelectric transducer) disposed at the bottom of the reservoir 1F. When energized, the vaporizer 30F can atomize the liquid in the reservoir 1F, thereby generating a mist that is emitted through the central opening 15F of the cover 52F, as described herein. In some embodiments, the mist generated by the vaporizer 30F passes through the liquid in the reservoir 1F to reach the upper surface of the liquid and fill the air space above the liquid with mist. As discussed herein, the diffuser system 100F can include a fan 26B (FIG. 3) that is adapted to push the mist or vapor out of the diffuser system 100F. In some embodiments, the reservoir 1F can include a mixer (not shown) disposed within the reservoir 1F. The mixer can be adapted to mix the essential oil with the foundation liquid. The mixer can mix the essential oil with the foundation before, during, or after operation of the vaporizer 30F. In some embodiments, the vaporizer 30F itself is adapted to mix the essential oil with the foundation liquid.

Figure 22A:
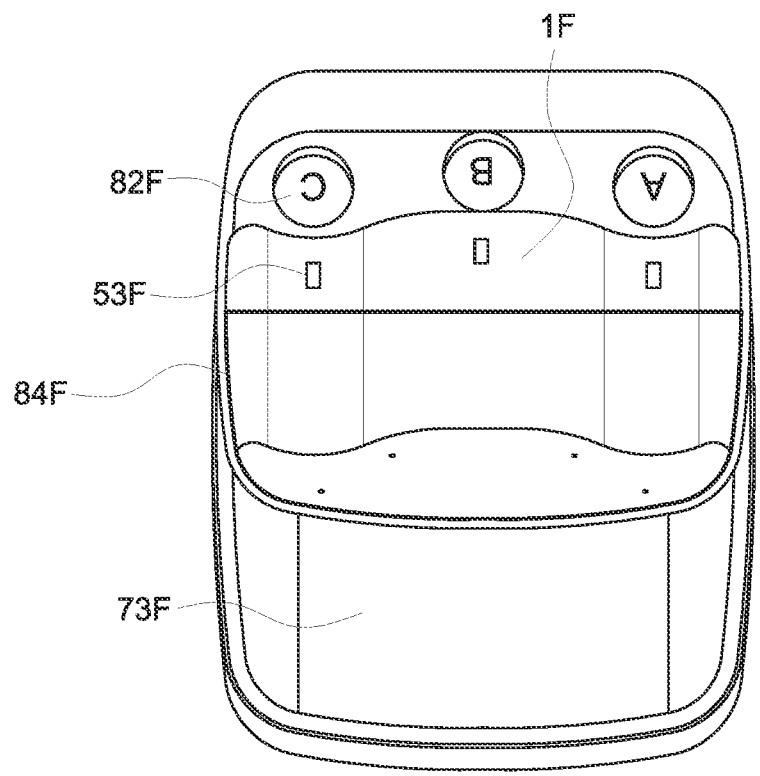
FIG. 22A shows a top view of a base portion of an essential oil diffuser system of having a removable reservoir insert.

FIG. 22A shows a top view of a base 73F, illustrating that the diffuser system 100F can include a removable insert 84F. The removable insert 84F can hold the foundation liquid (e.g. water). The spout 53F can be adapted to drop essential oil into the removable insert 84F so that the essential oil mixes with the foundation liquid contained in the removable insert 84F. The removable insert 84F can simplify cleaning the diffuser system 100F by allowing a user to remove the removable insert 84F and dump out the liquid therein and rinse out the removable insert 84F. In the illustrated embodiment, the removable insert 84F has a top lip that sits under the spouts 53F. In some embodiments, the removable insert 84F can include through holes that align with the spouts 53F or corresponding through holes on the base 73F to form a passage way by which essential oil can flow into the foundation liquid contained within the removable insert 84F when the removable insert 84F is seated into the base 73F. In some embodiments, the spouts 53F are spring loaded and align with corresponding slots disposed on the insert 84F. The spring-loaded spouts 53F can move into the base 73F to allow the insert 84F to move past the spout 53F as the insert is inserted or removed from the base 84F.

Figure 22B:
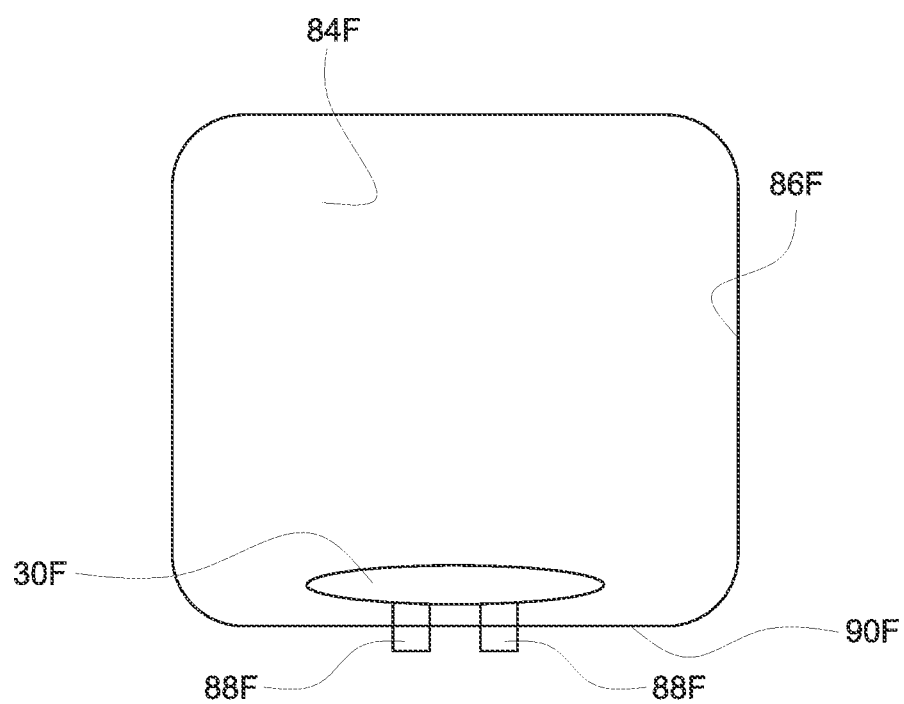
FIG. 22B shows a side cross-sectional view of an embodiment of a removable reservoir insert.

FIG. 22B depicts a side cross-sectional view of the removable insert 84F. The removable insert 84F can include the vaporizer 30F. The vaporizer 30F can be disposed on or at an inner surface 86F of the removable insert 84F. The vaporizer 30F can be electrically coupled to conductive strips 88F that are disposed on an outer bottom surface 90F of the removable insert 84F. When the insert 84F is seated into the base 73F, the conductive strips 88F can align with corresponding electrical conductors (not shown) disposed on the base 73F, making an electrical connection that allows an electrical component (e.g. circuit) within the base 73F to power the vaporizer 84F. In this way, the base 73F can include electrical wiring that supports the actuation and control of the vaporizer 30F.

Figure 23A:
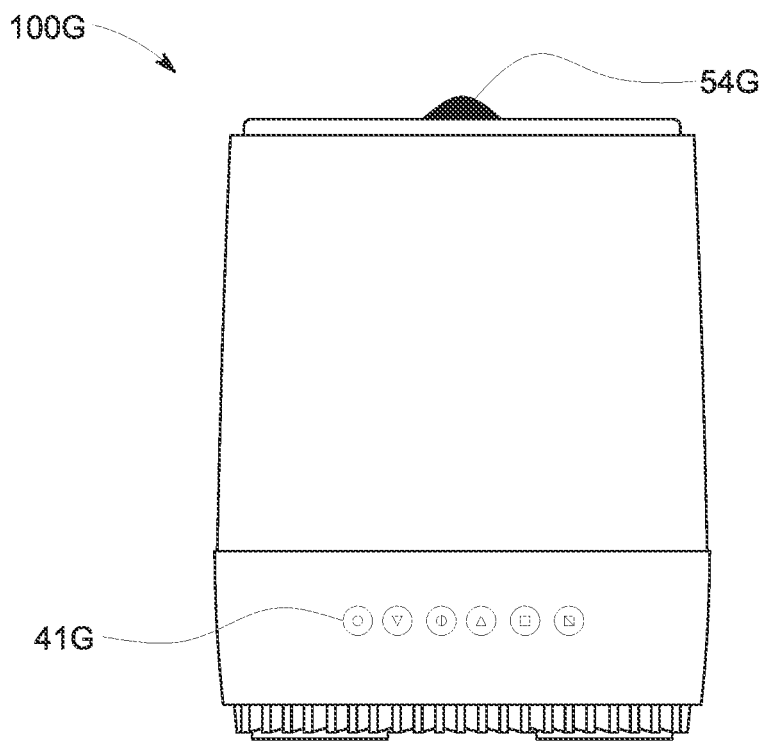
FIG. 23A shows a front view of an embodiment of the essential oil diffuser system of the present disclosure.
Figure 23B:
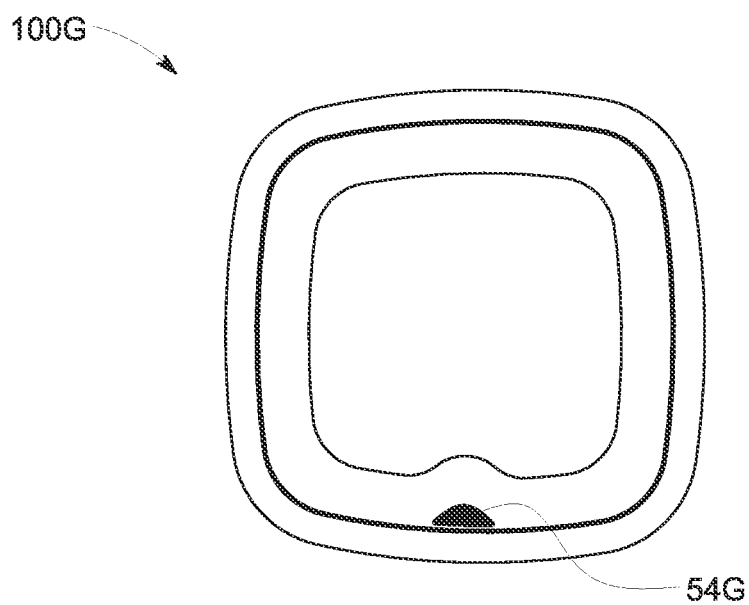
FIG. 23B shows a top view of the essential oil diffuser system of FIG. 23A.
Figure 23C:
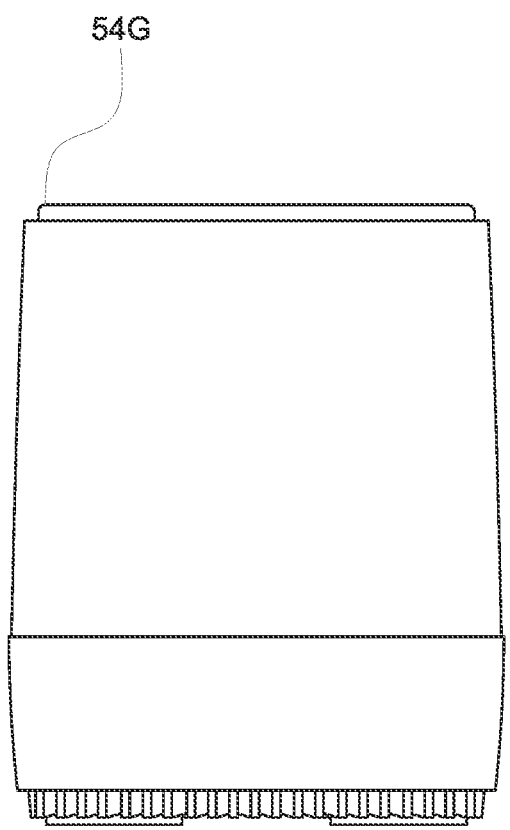
FIG. 23C shows a side view of the essential oil diffuser system of FIG. 23A.

FIGS. 23A-C illustrate another embodiment of a diffuser system 100G similar to the diffuser system 100 except as described differently below. FIG. 23A shows a front view of the diffuser 100G, illustrating that the diffuser 100G can include interface buttons 41G, as discussed herein. FIG. 23B is a top view of the diffuser system 100G, illustrating the diffuser system 100G can include an output nozzle 54G disposed near a front edge of the diffuser system 100G. FIG. 23C is a right side view of the diffuser system 100G, illustrating a curved profile of the output nozzle 54G.

Figure 24A:
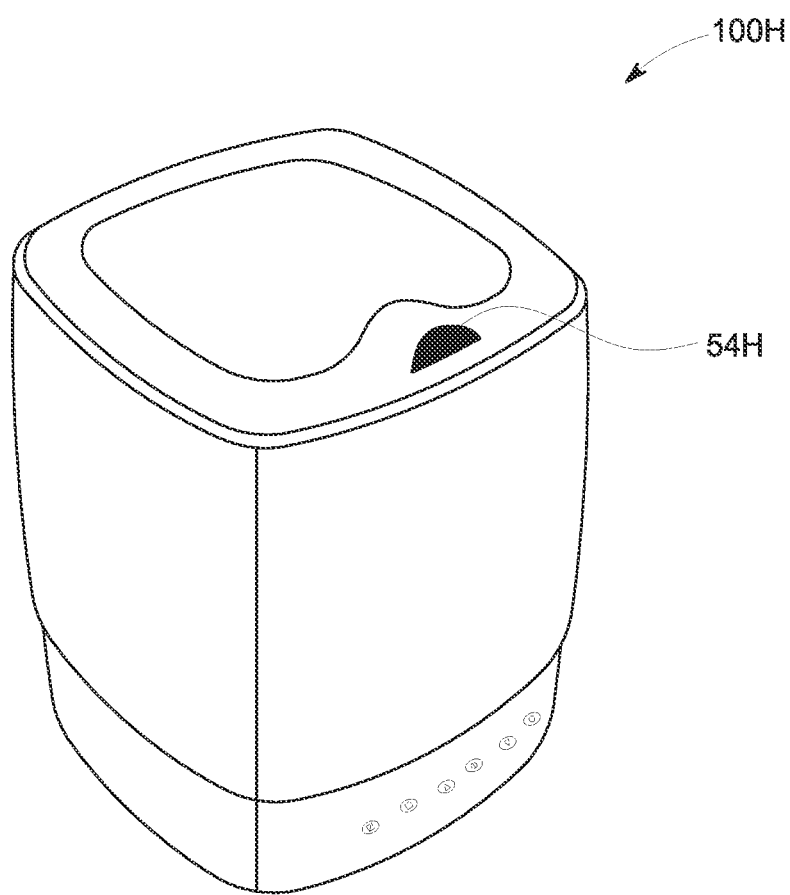
FIG. 24A shows a perspective view of an embodiment of the essential oil diffuser system of the present disclosure.
Figure 24B:
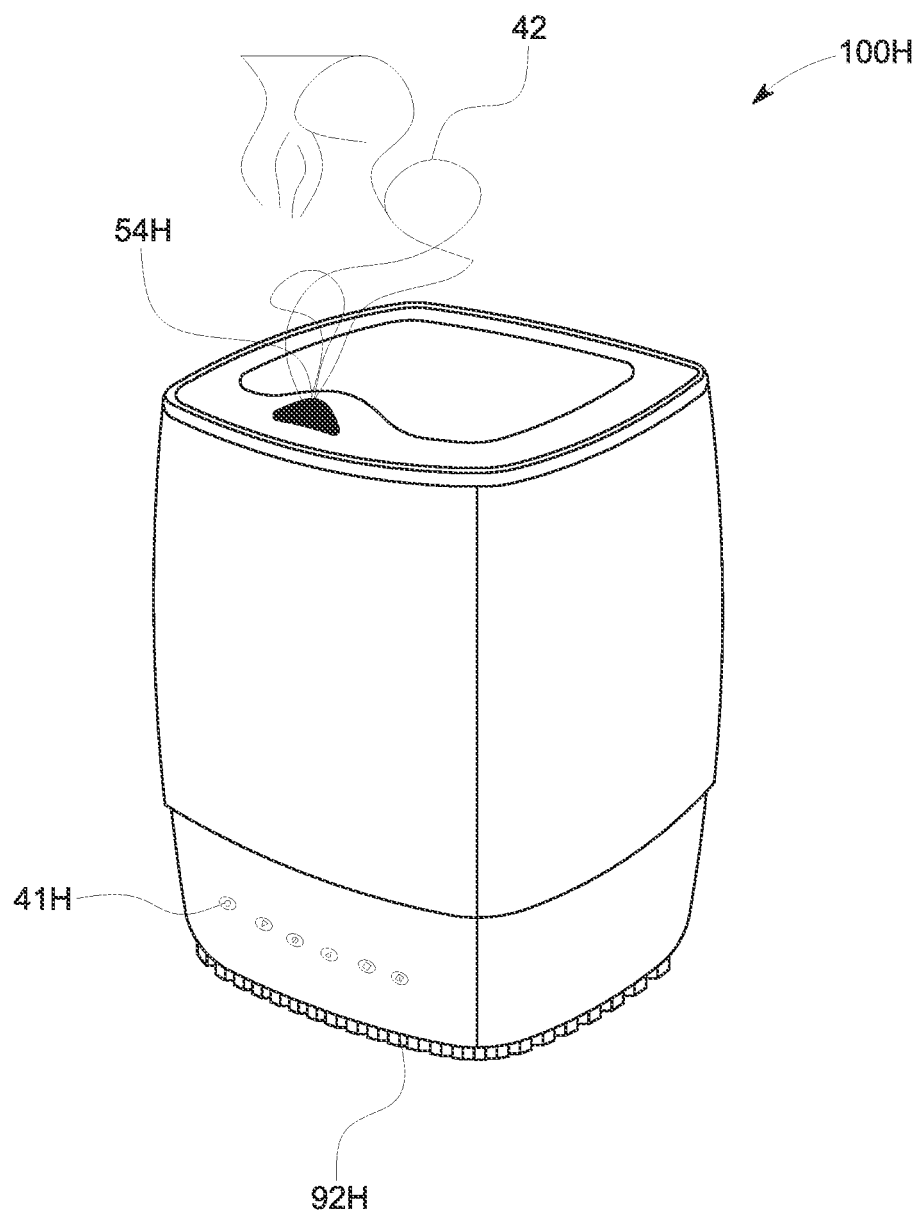
FIG. 24B shows a partial front view of the essential oil diffuser system of FIG. 24A.

FIGS. 24A-B illustrate another embodiment of a diffuser system 100H similar to the diffuser system 100 except as described differently below. FIG. 24B shows a front view of the diffuser 100H, illustrating that the diffuser 100H can include interface buttons 41H, as discussed herein. The diffuser system 100H can include vents 92H that allow a fan of the diffuser system 100H to draw in air. The fan can be adapted to push the vapor 42 out of the output nozzle 54H of the diffuser system 100H, as discussed herein.

Figure 25:
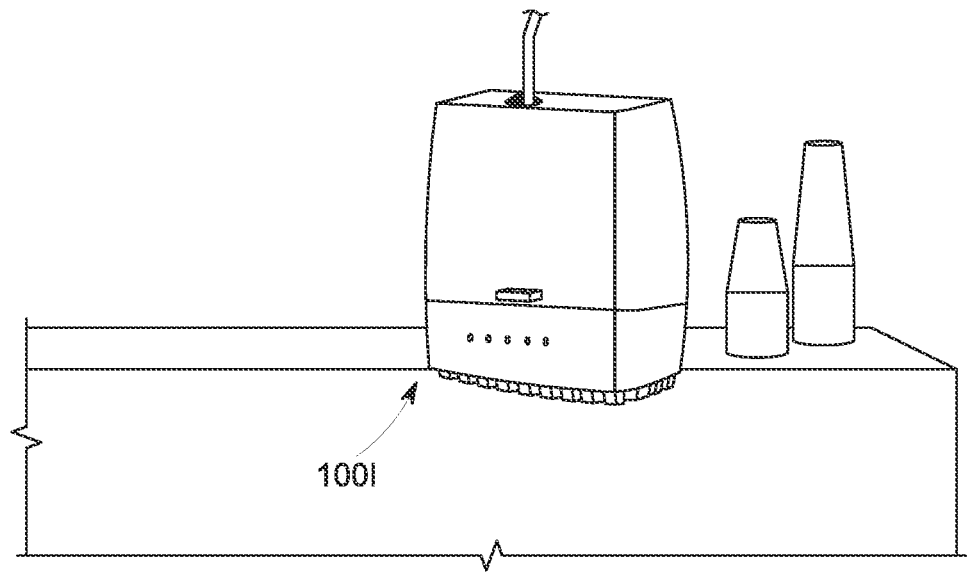
FIG. 25 shows an embodiment of the essential oil diffuser system of the present disclosure.

FIG. 25 illustrates another embodiment of a diffuser system 100I similar to the diffuser system 100. In use, the diffuser system 100I can be placed on a table, a shelf, or other suitable location of a room.

Figure 26:
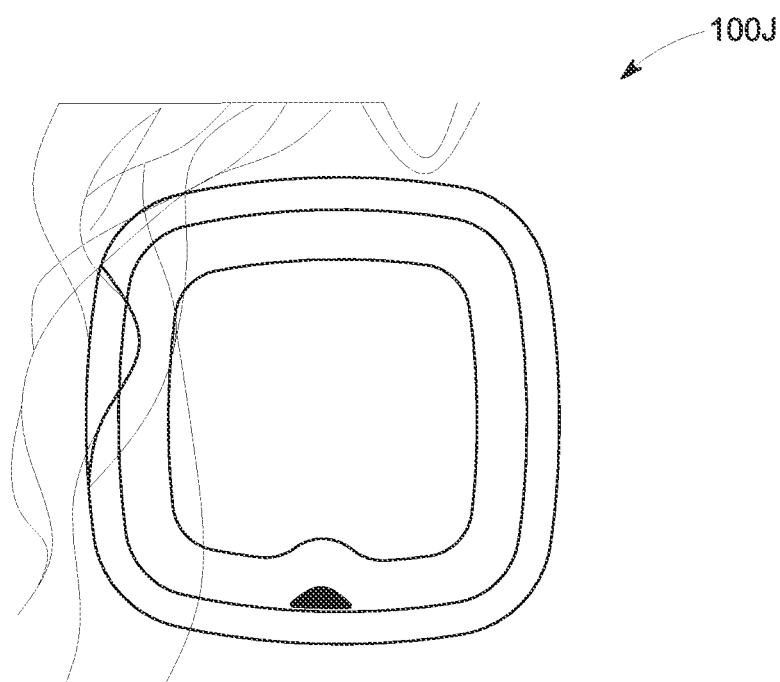
FIG. 26 shows a top view of an embodiment of the essential oil diffuser system of the present disclosure.

FIG. 26 illustrates a top view of another embodiment of a diffuser system 100J similar to the diffuser system 100.

The computer, computer chips and computer devices described above may be embodied by a processor (or processors) and computer-readable memory in one or more components discussed above. The phrases referencing specific computer-implemented processes and functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Likewise the term "and/or" in reference to a list of two or more items, covers all of the following interpretations of the word: anyone of the items in the list, all of the items in the list, and any combination of the items in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

The invention claimed is:

1. A home health device comprising:
   a housing;
   a reservoir, within the housing, adapted to hold a foundation liquid consisting of water;
   at least one dock adapted to receive at least one container containing a concentrate liquid different from the foundation liquid;
   an atomization chamber, within the housing, receiving a vaporization liquid, the vaporization liquid being formed from at least a portion of the foundation liquid from the reservoir and a portion of the concentrate liquid from the at least one container;
   a vaporizer configured vaporize at least a portion of the vaporization liquid; and
   a duct providing a fluid flow path between the housing and an airspace that surrounds the device,
   wherein the concentrate liquid is delivered from the at least one container to the atomization chamber at a location above a top surface of atomization chamber fluid therein.

2. The home health device of claim 1, wherein the reservoir and the atomization chamber are a single chamber.

3. The home health device of claim 1, wherein the concentrate liquid includes at least one of a fragrance, an essential oil, chemicals and medicine.

4. The home health device of claim 1, further comprising a drop control mechanism disposed between the dock and the vaporizer, the drop control mechanism configured to drop-wise regulate a flow of the concentrate liquid from the at least one container into the vaporizer.

5. The home health device of claim 4, wherein the drop control mechanism is operable to measure a predetermined amount of the concentrate liquid into the vaporizer.

6. The home health device of claim 5, wherein the predetermined amount of the concentrate liquid provides an amount of a medicine predisposed in the concentrate liquid.

7. The home health device of claim 1, further comprising a sensor for detection when the at least one container at the at least one dock is empty.

8. The home health device of claim 7, further comprising a container indicator for providing a visual indication when the sensor detects that the at least one container is empty.

9. The home health device of claim 1, further comprising a reservoir liquid sensor for determining if the reservoir is empty.

10. The home health device of claim 1, further comprising a software application configured to communicate with the device, the software application including at least one module, written in computer code stored on a non-transitory computer media, the at least one module configured to receive, from a user a desired recipe for delivery of the concentrate liquid, and send a signal to the device to operate a drop control mechanism for the concentrate liquid to deliver an appropriate volume of the concentrate liquid into the atomization chamber.

11. The home health device of claim 10, wherein the at least one module is further configured to receive an indication, from the device, when the at least one container containing the concentrate liquid is empty.

12. The home health device of claim 10, wherein the at least one module is further configured to alert the user to operate a cleaning cycle after a predetermined number of distributions of the concentrate liquid or after a predetermined period of time, wherein the cleaning cycle is performed by the home health device.

13. The home health device of claim 1, further comprising at least one drop control mechanism operable to transfer the concentrate liquid from the at least one container to the location above the top surface of the atomization chamber fluid in the atomization chamber, wherein the at least one drop control mechanism operates in a reverse direction after delivery of the concentrate liquid to the atomization chamber.

14. The home health device of claim 13, further comprising a sensor detecting a presence or an absence of the concentrate liquid exiting the location above the atomization chamber fluid in the atomization chamber, wherein the absence of the concentrate liquid while the at least one drop control mechanism is operating provides an indication of the at least one container being empty.

15. The home health device of claim 1, further comprising at least one dispensing button operable to release, into the atomization chamber, a predetermined amount of concentrate liquid from a respective one of the at least one container.

* * * * *